United States Patent [19]
Hirai et al.

[11] Patent Number: 6,127,149
[45] Date of Patent: *Oct. 3, 2000

[54] MODIFIED EPIMORPHIN

[75] Inventors: Yohei Hirai; Shogo Koshida; Yumiko Oka, all of Kanagawa, Japan

[73] Assignee: Sumitomo Electric Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/493,071

[22] Filed: Jun. 21, 1995

[30] Foreign Application Priority Data

Jun. 21, 1994 [JP] Japan ................................ 6-162874
Mar. 31, 1995 [JP] Japan ................................ 7-099979
Mar. 31, 1995 [JP] Japan ................................ 7-099980

[51] Int. Cl.$^7$ ........................... C12N 15/12; C12N 15/63; C12N 5/00; C07K 14/435
[52] U.S. Cl. .................... 435/69.7; 435/69.1; 435/252.3; 435/325; 435/320.1; 530/350; 536/23.4; 536/23.5
[58] Field of Search ................ 536/23.4, 23.5; 435/69.1, 69.7, 325, 252.3, 320.1; 530/350

[56] References Cited

FOREIGN PATENT DOCUMENTS 0 562 123 A1  9/1993  European Pat. Off. .
6-25295  2/1994  Japan .

OTHER PUBLICATIONS

Uhlen et al., Methods in Enzymology, vol. 185, pp. 129–143, 1990.
Hirai, Eur. J. Biochem. 225, 1133–1139, Nov. 1990.
Hirai et al.—Epimorphin: A Mesenchymal Protein Essential for Epithelial Morphogenesis—Cell, vol. 69, 471–481, May 1, 1992.
"PCR Protocols", by Russel Higuchi, Harcourt Brace Javanovich Japan Inc., 1991.
"Experimental Medicine", by Katsuhisa Nakajima, Yodosha Co., Ltd., vol. 8, No. 9, 1990.
"Vectors for Selective Expression of Cloned DNAs by T7 RNA Polymerase", by Alan H. Rosenberg et al., *Gene*, vol. 56, 1987.
"Laboratory–Manual Gene Engineering", Maruzen Co., Ltd., 1988.
"A Method for Random Mutagnesis of a Defined DNA Segment Using a Modified Polymerase Chain Reaction", by David W. Leung et al., *Technique—A Journal of Methods in Cell and Molecular Biology*, vol. 1, No. 1, 1989.

*Primary Examiner*—Gary L. Kunz
*Assistant Examiner*—Christine Saoud
*Attorney, Agent, or Firm*—McDermott, Will & Emery

[57] ABSTRACT

Disclosed herein are a modified epimorphin obtained by adding a hydrophilic peptide composed of 5 to 99 amino acids to at least one terminus of a polypeptide containing the functional domain of epimorphin, and a modified epimorphin composed of a polypeptide having a structure wherein a hydrophobic domain adjacent to the C-terminus of the whole-length epimorphin consisting of a coiled coil domain (1) on the N-terminal side, a functional domain (2) at the center, a coiled coil domain (3) on the C-terminal side and the hydrophobic domain (4) adjacent to the C-terminus has been deleted from the whole-length epimorphin, and at least part of amino acids have been deleted from the terminal side of at least one of the coiled coil domains (1) and (3) as well. The invention also discloses a variant modified epimorphin obtained by making partial substitution, deletion and/or insertion of amino acids in the amino acid sequence of the modified epimorphin, wherein the variant maintains the function of the original sequence. The invention further discloses DNAs encoding the modified epimorphin and variant thereof, recombinant vectors containing the DNAs, transformants obtained by introducing the recombinant vectors, and a production method of the modified epimorphin and the variants thereof making use of the transformant.

64 Claims, 3 Drawing Sheets

MODIFIED EPIMORPHIN

FIELD OF THE INVENTION

The present invention relates to a modified epimorphin obtained by modifying epimorphin, which is a polypeptide existing in mesenchymal cells and controlling the morphogenesis of epithelial tissue, or a fragment thereof, and more particularly to a modified epimorphin obtained by modifying epimorphin, which is useful in elucidating the attack mechanism of diseases caused by the morphogenetic abnormality of epithelial tissue and developing diagnosis and medical treatment for these disease and remedies for wounds, or a fragment thereof while keeping its activity, and variants (variant modified epimorphin polypeptides) obtained by making partial substitution, deletion and/or insertion of amino acids in the amino acid sequence of the modified epimorphin.

The present invention also relates to DNAs encoding such a modified epimorphin and variants thereof, recombinant vectors containing the DNAs, transformants obtained by introducing the recombinant vectors, and a production method of the modified epimorphin and the variants thereof making use of the transformant.

In the present invention, the term "modified epimorphin" means a fragment or polypeptide of epimorphin, which is obtained by modifying the epimorphin or a fragment thereof.

BACKGROUND OF THE INVENTION

Since the normal organization and morphogenesis of epithelial tissue are under some control of a factor originating in mesenchymal cells, and diseases attributable to the morphogenetic abnormality of the epithelial tissue may be often caused by the mesenchymal cells present around the tissue, studies on the mechanism of mesenchymal cells which support the morphogenesis of the epithelial tissue have been made time. Although studies on the isolation, purification and structural analysis of a molecule, which controls the morphogenesis of the epithelial tissue, have been extensively made throughout the world, however, its substance has been scarcely known under the circumstances because the object of study is a substance which expresses under restrictions of time and space in a complicated system, and so it is difficult to produce a simplified experimental system.

In order to realize the elucidation of diseases caused by the morphogenetic abnormality of the epithelial tissue and the attack mechanism thereof, and the development of medical treatments for these diseases, it was an indispensable premise to isolate and purify such a molecule, which controls the morphogenesis of the epithelial tissue, and make the structure thereof clear. Therefore, an important problem in the art was to achieve the elucidation of the structure of such a molecule, and the like.

In such circumstances, the present inventors recently succeeded in isolation and identification of a molecule (the present inventors termed it "epimorphin") which controls the morphogenesis of the epithelial tissue (Japanese Patent Application Laid-Open No. 25295/1994). Epimorphin is a physiologically active substance comprising, as a core protein, a protein composed of 277 to 289 amino acids and is principally biosynthetically produced by mesenchymal cells.

The present inventors succeeded in determining the amino acid sequences of human and mouse epimorphin molecules. The splicing of their genes has revealed that at least three types exist in respective epimorphin molecules. The human epimorphin molecules include three types, human epimorphin represented by SEQ ID NO. 1, human epimorphin (isoform A) represented by SEQ ID NO. 2 and human epimorphin (isoform B) represented by SEQ ID NO. 3, all shown in SEQUENCE LISTING, which will be described subsequently. The mouse epimorphin molecules include three types, mouse epimorphin represented by SEQ ID NO. 4, mouse epimorphin (isoform A) represented by SEQ ID NO. 5 and mouse epimorphin (isoform B) represented by SEQ ID NO. 6, all shown in the SEQUENCE LISTING. The human epimorphin molecules and the mouse epimorphin molecules have homology of about 90% with each other at the amino acid level. Therefore, they are well conserved even between different animal species.

However, these epimorphin molecules involved a problem that since they firmly bind to a cell membrane at a domain (hereinafter referred to as "the C-terminal hydrophobic domain") adjacent to the C-terminus thereof, which is extremely high in hydrophobic nature, while taking a complex high-order structure in the living body so as to perform their functions, they are extremely difficult to prepare while keeping the activity of epimorphin at a high level. In particular, the epimorphin and the isoform A markedly show such a tendency. When a cell membrane-binding domain exists, it is difficult to secrete epimorphin produced by cultured animal cells into a medium so as to isolate and purify it. The present inventors proposed the preparation of a soluble modified epimorphin by a process of removing the C-terminal hydrophobic domain, and the like (Japanese Patent Application Laid-Open No. 25295/1994). However, these processes have been so far insufficient in the compatibility of the maintenance of high activity with the solubility, and there has hence been a demand for development of a more improved process.

If a modified epimorphin easy to prepare and purify can be obtained while keeping the physiological activity of epimorphin, it is useful in elucidating the attack mechanism of diseases caused by the morphogenetic abnormality of the epithelial tissue and developing medical treatments for these diseases.

OBJECT AND SUMMARY OF THE INVENTION

It is an object of the present invention to provide a modified epimorphin which keeps the high activity of epimorphin and is easy to prepare and purify.

The present inventors have analyzed the constitutive amino acids of epimorphin by a computer. As a result, it has been found that epimorphin is roughly divided into four structurally-characteristic domains as illustrated in FIG. 1. More specifically, an epimorphin polypeptide can be divided into a coiled coil domain (1), a functional domain (2), another coiled coil domain (3) and a C-terminal hydrophobic domain (4) from the N-terminal side thereof. The two coiled coil domains can be further divided into some subdomains (for example, heptad repeats and other domains).

The present inventors have also found that when a hydrophilic peptide composed of 5 to 99 amino acids is added to the N-terminus and/or C-terminus of a polypeptide containing the functional domain (2) of epimorphin, a modified epimorphin which keeps the high activity of epimorphin and can be easily purified and provided.

The present inventors have further found that when at least part of the coiled coil domains (1) and (3) are deleted from an epimorphin polypeptide from which the C-terminal hydrophobic domain has been deleted, its physiological activity can be enhanced, and consequently, the balance between the physiological activity and the solubility can be adjusted according to one's desire. According to this method, a modified epimorphin useful for the development of diagnosis and medical treatment for diseases caused by the morphogenetic abnormality of epithelial tissue, or the development of novel remedies for wounds and the like can be obtained without adversely affecting the high-order structure and activity of epimorphin.

The present invention has been led to completion on the basis of these findings.

According to the present invention, there is thus provided a modified epimorphin obtained by adding a hydrophilic peptide composed of 5 to 99 amino acids to at least one terminus of a polypeptide containing the functional domain of epimorphin.

According to the present invention, there is also provided a modified epimorphin composed of a polypeptide having a structure that a hydrophobic domain adjacent to the C-terminus of the whole-length epimorphin consisting of a coiled coil domain (1) on the N-terminal side, a functional domain (2) at the center, a coiled coil domain having a structure wherein: (i) A hydrophobic domain of the C-terminal region of the whole-length epimorphin has been deleted from the whole length epimorphin, and (ii) At least part of the amino acids have been deleted from the terminal side of at least one of the coiled coil domains 1 and 3.

This modified epimorphin may be a variant (variant modified epimorphin) obtained by making partial substitution, deletion and/or insertion of amino acids in the amino acid sequence thereof.

According to the present invention, there are further provided DNAs encoding the modified epimorphin and variant thereof, recombinant vectors containing the DNAs, transformants obtained by introducing the recombinant vectors, and a production method of the modified epimorphin and the variants thereof making use of the transformant.

DETAILED DESCRIPTION OF THE PREFERRED EMBODIMENTS

Features of the present invention will hereinafter be described in detail.

Epimorphin is a mesenchymal cell membrane molecule essential for the morphogenesis of epithelia in the fetal period and is also considered to participate in the construction of vital tissues. Epimorphin is a membrane protein identified as an antigen molecule recognized by a monoclonal antibody MC-1, which inhibits the normal morphogenesis of epithelia in various fetal tissues [Cell, Vol. 69, p. 471–481 (1992)].

Epimorphin is a protein (molecular weight: about 33 kDa) composed of about 280 amino acids. As human epimorphin molecules, there have been known epimorphin represented by SEQ ID NO. 1, epimorphin isoform A represented by SEQ ID NO. 2 and epimorphin isoform B represented by SEQ ID NO. 3, all shown in the SEQUENCE TABLE. As mouse epimorphin molecules, there have been known epimorphin represented by SEQ ID NO. 4, epimorphin isoform A represented by SEQ ID NO. 5 and epimorphin isoform B represented by SEQ ID NO. 6, all shown in the SEQUENCE TABLE. The mouse epimorphin is useful in, for example, elucidating the attack mechanism of diseases caused by the morphogenetic abnormality of the epithelial tissue making use of model animals. The human epimorphin is useful in, for example, diagnosing and treating such diseases.

Epimorphin exists in mesenchymal cells around the epithelial tissue and has a function of controlling the morphogenesis of the epithelial tissue, and the like. Such an epimorphin firmly binds to a cell membrane at a C-terminal hydrophobic domain in its molecule while taking a complex stereostructure so as to perform its functions. The predicted product of cDNA of epimorphin is a molecule having a molecular weight of about 33 kDa. It has been already revealed that this molecule forms a plurality of SDS-resistant complexes in the living body, and that of these, an extracellular substance having a molecular weight of about 150 kDa is recognized by the monoclonal antibody MC-1.

Figure 1:
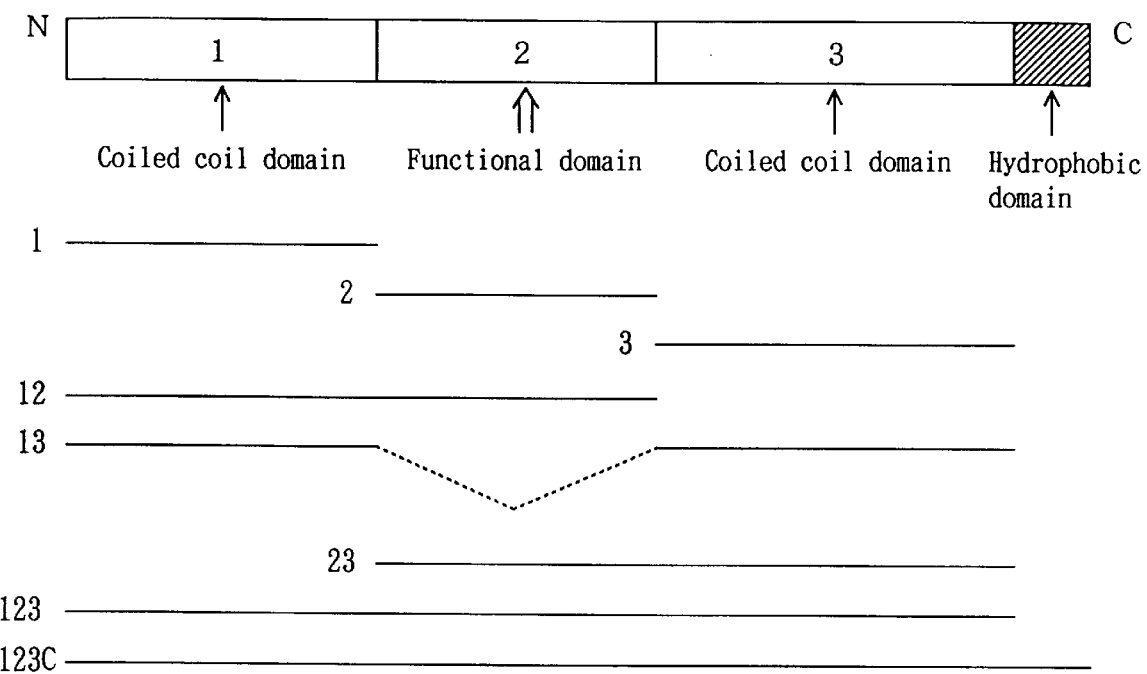
FIG. 1 illustrates the structural feature of epimorphin and the design of its fragments.
Figure 5:
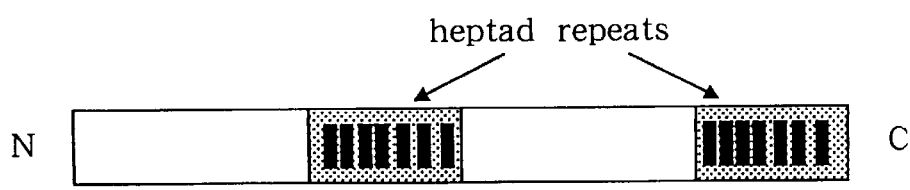
FIG. 5 illustrates the structural feature of an epimorphin fragment (1).

According to an analysis by a computer, epimorphin can be roughly divided into 4 domains in structure as illustrated in FIG. 1. The domains other than the C-terminal hydrophobic domain (transmembrane domain) are composed of fragments [coiled coil domains (1) and (3)] on the N-terminal and C-terminal sides, which are easy to take the so-called coiled coil structure with hydrophobic amino acids forming regular lines (heptad repeats), and a central fragment (2) between them, which has substantially the same size as the former fragments. The coiled coil domains (1) and (3) can be each divided into 4 subfragments including 2 heptad repeats. For reference, the detailed structure of the fragment (1), which is a coiled coil domain, is illustrated in FIG. 5.

According to the results of the study carried out by the present inventors, the central fragment (2) has been found to be a functional domain. The fact that the central fragment (2) of epimorphin is the functional domain can be judged from its reactivity with the monoclonal antibody MC-1 and cellular adhesiveness. As illustrated in FIG. 1, the fragments (1), (2), (3), (12), (13), (23), (123) and (123C: the whole-length epimorphin) were separately prepared with *Escherichia coli* in accordance with the method known per se in the art to determine their reactivity with the monoclonal antibody MC-1 which binds to the functional site of epimorphin. In particular, the fragments (2) and (23) showed strong reactivity (see Referential Example 1). Since the monoclonal antibody inhibits the activity of the extracellular epimorphin in the living body, this central fragment (2) is considered to be closely related to the activity of epimorphin. The cellular adhesiveness can be determined by, for example, coating dishes (not subjected to a treatment for cell culture) with solutions of the respective fragments in 8 M urea, thoroughly washing the dishes with 8 M urea and PBS (phosphate-buffered saline) to thinly and evenly spread the fragments on the dishes, and then seeding epithelial cells on the dishes to determine their responsibility to the fragments. As a result, it has been found that the epithelial cells rapidly adhere only to the dish coated with the central fragment (2). In addition, it has also been found that the adhering phenomenon of the central fragment (2) to the epithelial cells is inhibited by the addition of the monoclonal antibody MC-1. Namely, it has been revealed that the domain of the central fragment (2) directly act on the cells.

Accordingly, it is apparent that the central fragment (2) is the functional domain of epimorphin. Epimorphin and fragments (polypeptides) containing this functional domain are expected to apply to various uses making good use of the epimorphin activity thereof. However, some of epimorphin and the functional domain-containing fragments may be of low solubility or insoluble in physiological solutions. When a polypeptide containing the functional domain of epimorphin is hardly soluble or insoluble in physiological solutions, for example, it is difficult to secrete such a polypeptide produced by cultured animal cells into a medium so as to isolate and purify it, and its handling and development to various applications also become difficult.

According to the present invention, a hydrophilic peptide composed of 5 to 99 amino acids is added to at least one terminus of a polypeptide containing the functional domain of epimorphin, whereby a modified epimorphin which keeps the high activity of epimorphin and is soluble in physiological solutions can be obtained.

According to the results of the analysis of the amino acid sequence of epimorphin by a computer, in the case of the human epimorphin, the functional domain of epimorphin has been found to be a domain containing an amino acid sequence ranging from the 99th amino acid (phenylalanine) to the 189th amino acid (glutamine) from the N-terminus in common to the epimorphin, the epimorphin isoform A and the epimorphin isoform B. Later, the results of a further investigation as to the human epimorphin have revealed that even a domain containing an amino acid sequence ranging from the 104th amino acid to the 187th amino acid from the N-terminus shows the epimorphin activity. Therefore, the functional domain in the human epimorphin is a domain containing an amino acid sequence ranging from the 99th amino acid to the 189th amino acid, preferably from the 104th amino acid to the 187th amino acid from the N-terminus of the whole-length epimorphin.

In the case of the mouse epimorphin, the functional domain of epimorphin has been found to be a domain containing an amino acid sequence ranging from the 100th amino acid (cysteine) to the 190th amino acid (glutamine) from the N-terminus in common to the epimorphin, the epimorphin isoform A and the epimorphin isoform B. Later, the results of a further investigation as to the mouse epimorphin have revealed that even a domain containing an amino acid sequence ranging from the 105th amino acid to the 188th amino acid from the N-terminus shows the epimorphin activity. Therefore, the functional domain in the mouse epimorphin is a domain containing an amino acid sequence ranging from the 100th amino acid to the 190th amino acid, preferably from the 105th amino acid to the 188th amino acid from the N-terminus of the whole-length epimorphin.

Modified Epimorphin Obtained by Adding a Hydrophilic Peptide to at Least One Terminus of a Polypeptide Containing the Functional Domain of Epimorphin No particular limitation is imposed on the polypeptide containing the functional domain of epimorphin so far as it contains the central domain of the epimorphin molecule, which is a functional domain. Such a polypeptide may have any length within limits of epimorphin. For example, a polypeptide composed of the whole-length epimorphin may be included. In general, it is however preferable from the viewpoints of solubility and activity that the C-terminal hydrophobic domain (a domain composed of 23–24 amino acids) be deleted from the whole-length epimorphin. It is also preferable that at least part of amino acids (amino acid residues or peptide) in the coiled coil domain (1) on the N-terminal side, which the domain forms to mask the activity of the functional domain, be deleted from the whole-length epimorphin according to the kind of the hydrophilic polypeptide to be added. In order to obtain a modified epimorphin high in solubility and easy to handle, it is desirable that at least part of amino acids in the coiled coil domain (3) on the C-terminal side be deleted from the whole-length epimorphin. At least parts of amino acids in the coiled coil domains (1) and (3) on both N-terminal and C-terminal sides may be deleted.

In particular, when amino acids in the coiled coil domain (1) on the N-terminal side of epimorphin are deleted from the N-terminal side, the epimorphin activity of the resulting fragment shows a tendency to enhance. In order to obtain a modified epimorphin higher in activity, therefore, it is preferable that at least part of amino acids in the coiled coil domain (1) on the N-terminal side of epimorphin be deleted from the whole-length epimorphin from the N-terminal side. On the other hand, when amino acids in the coiled coil domain (1) are deleted from the N-terminal side, the solubility of the resulting fragment in physiological solutions shows a tendency to be reduced. However, the addition of the hydrophilic peptide to at least one terminus of such a fragment makes it possible to enhance the solubility of the fragment while keeping high activity.

In the case of the human epimorphin, the coiled coil domain (1) is a domain ranging from the N-terminus to the 103rd amino acid in the whole-length epimorphin. Fragments obtained by deleting in a range of from 1 to 28 amino acids in such a domain from the N-terminal side can keep good solubility and have enhanced epimorphin activity. Fragments obtained by deleting in a range of from 29 to 77 amino acids, further, from 29 to 103 amino acids in such a domain from the N-terminal side can exhibit higher activity. A domain ranging from the 29th amino acid to the 103th amino acid from the N-terminus contains heptad repeats and is particularly easy to erect a coiled coil structure. In a range of from 30 to 98 amino acids from the N-terminal side may be deleted. In any case, it is preferable to delete the C-terminal hydrophobic domain.

In the case of the mouse epimorphin, the coiled coil domain (1) is a domain ranging from the N-terminus to the 104th amino acid in the whole-length epimorphin. Fragments obtained by deleting in a range of from 1 to 29 amino acids in such a domain from the N-terminal side can keep good solubility and have enhanced epimorphin activity. Fragments obtained by deleting in a range of from 30 to 78 amino acids, further, from 30 to 104 amino acids in such a domain from the N-terminal side can exhibit higher activity. A domain ranging from the 30th amino acid to the 104th amino acid from the N-terminus contains heptad repeats and is particularly easy to erect a coiled coil structure. In a range of from 30 to 99 amino acids from the N-terminal side may be deleted. In any case, it is preferable to delete the C-terminal hydrophobic domain.

The coiled coil domain (3) is a domain obtained by removing the coiled coil domain (1), the functional domain (2) and the C-terminal hydrophobic domain from the whole-length epimorphin and varies according to the species and isoforms of the epimorphin. When the coiled coil domain (3) in the epimorphin other than the isoforms is deleted, it is generally preferable that in a range of from 25 to 99 amino acids be deleted from the whole-length epimorphin from the C-terminal side.

The hydrophilic peptide to be added to the polypeptide containing the functional domain of epimorphin is a hydrophilic peptide of such a size that the solubility of the functional domain of epimorphin is improved and the exhibition of its function is not blocked. Specifically, it is a hydrophilic peptide composed of in a range of from 5 to 99 amino acids.

Amino acids can be roughly divided into hydrophilic amino acids and hydrophobic amino acids. The hydrophilic amino acids include glycine (Gly), threonine (Thr), tryptophan (Trp), serine (Ser), tyrosine (Tyr), proline (Pro), histidine (His), glutamic acid (Glu), glutamine (Gln), aspartic acid (Asp), asparagine (Asn), lysine (Lys) and arginine (Arg). The hydrophobic amino acids include isoleucine (Ile), valine (Val), Leucine (Leu), phenylalanine (Phe), cysteine (Cys), methionine (Met) and alanine (Ala).

The hydrophilic peptide useful in the practice of the present invention is a peptide containing bound hydrophilic amino acids in a proportion of, generally, at least 50%, preferably, at least 60%, more preferably, at least 70% based on the number of amino acids. In order to embed the resulting modified epimorphin in vivo, a hydrophilic peptide low in antigenicity may preferably be selected from the viewpoint of safety. In the case where the resulting modified epimorphin is investigated in vitro, a hydrophilic peptide easy to detect may preferably be selected. In any case, it is desirable that the hydrophilic peptide be designed so as to contain such an amino acid sequence that the purification of the resulting modified epimorphin can be performed with ease.

When a hydrophilic peptide containing at least one amino acid sequence selected from the group consisting of, for example, the following amino acid sequences (a) to (h) is used where the in vitro investigation is performed, the resulting modified epimorphin can be detected with good reproducibility because an antibody having high sensitivity to such a hydrophilic peptide is easily available. Two or more of these amino acid sequences may be contained in a hydrophilic peptide.

(a) Tyr-Pro-Tyr-Asp-Val-Pro-Asp-Tyr-Ala (i.e., YPYDVPDYA), (SEQ ID NO. 21)

(b) Glu-Gln-Lys-Leu-Ile-Ser-Glu-Glu-Asp-Leu-Asn (i.e., EQKLISEEDLN), (SEQ ID NO. 22)

(c) Glu-Tyr-Lys-Glu-Glu-Glu-Glu-Lys (i.e., EYKEEEEK), (SEQ ID NO. 23)

(d) Tyr-Thr-Asp-Ile-Glu-Met-Asn-Arg-Leu-Gly-Lys (i.e., YTDIEMNRLGK), (SEQ ID NO. 24)

(e) Arg-Ile-Gln-Arg-Gly-Pro-Gly-Arg-Ala-Phe-Val-Thr-Ile-Gly-Lys (i.e., RIQRGPGRAFVTIGK), (SEQ ID NO. 25)

(f) Ala-Ser-Met-Thr-Gly-Gly-Gln-Gln-Met-Gly-Arg (i.e., ASMTGGQQMGR), (SEQ ID NO. 26)

(g) Gln-Pro-Glu-Leu-Ala-Pro-Glu-Asp-Pro-Glu-Asp (i.e., QPELAPEDPED), (SEQ ID NO. 27) and (h) Gly-Ala-Pro-Val-Pro-Tyr-Asp-Pro-Leu-Glu-Pro-Arg (i.e., GAPVPYDPLEPR) (SEQ ID NO. 28).

The size and kind of the hydrophilic peptide to be added to the N-terminus and/or the C-terminus of the polypeptide containing the functional domain of epimorphin may be freely chosen for combination as necessary for the intended application of the resulting modified epimorphin. Various kinds of modified epimorphin obtained by separately adding different hydrophilic peptides may be suitably mixed before use. If for example, at least five histidine (His) residues are consecutively contained in the hydrophilic peptide, the modified epimorphin prepared from this can be purified by one step through a column in which nickel has been fixed.

The hydrophilic peptide is added to the N-terminus, C-terminus or both termini of the polypeptide containing the functional domain of epimorphin. Whether the hydrophilic peptide is added to one terminus or to both termini can be suitably determined in view of the solubility of the polypeptide containing the functional domain of epimorphin in physiological solutions, the degree of epimorphin activity of the polypeptide, the kind of the hydrophilic peptide, and the like.

If the polypeptide containing the functional domain of epimorphin is composed of the whole-length epimorphin, the hydrophilic peptide may preferably be added to both termini thereof. If the polypeptide containing the functional domain of epimorphin is a fragment obtained by deleting the C-terminal hydrophobic domain, the hydrophilic peptide may preferably be added to either the N-terminal or both termini.

If the polypeptide containing the functional domain of epimorphin is a fragment obtained by deleting at least part of amino acids in the coiled coil domain (1) from the whole-length epimorphin from the N-terminal side, the hydrophilic peptide may preferably be added to either the N-terminal or both termini in order to avoid reduction in the solubility. Even if the polypeptide containing the functional domain of epimorphin is a fragment obtained by deleting at least part of amino acids in the coiled coil domain (1) from the whole-length epimorphin from the N-terminal side and moreover deleting the C-terminal hydrophobic domain, the hydrophilic peptide may also be preferably added to either the N-terminal or both termini.

If the polypeptide containing the functional domain of epimorphin is a fragment obtained by deleting the C-terminal hydrophobic domain and at least part of amino acids in the coiled coil domain (3) on the C-terminal side from the whole-length epimorphin, the hydrophilic peptide may preferably be added to either the C-terminal or both termini.

As a method of adding the hydrophilic peptide to one or both termini of the polypeptide containing the functional domain of epimorphin, there may be used various techniques such as biochemical techniques and gene engineering techniques. As an example of a method making use of a biochemical technique, may be mentioned a process in which an epimorphin molecule itself is chemically or physically cleaved to obtain a fragment containing the functional domain, the fragment is purified, a hydrophilic peptide is then bound to the N-terminus and/or C-terminus of the fragment making use of a chemical reaction.

As an example of a method making use of a gene engineering technique, may be mentioned a process in which a part of a gene encoding epimorphin and a gene encoding a hydrophilic peptide to be added are integrated into an appropriate vector to express a modified epimorphin in a host. As a specific technique, there may be used, for example, the following simple technique.

cDNA (A) encoding a fragment containing the functional domain of epimorphin is first synthesized by polymerase chain reaction (PCR). On the other hand, single-stranded DNAs (B and C), in which DNA encoding a hydrophilic peptide to be added to the N-terminus and/or C-terminus of the above fragment are joined to 10 to 20 bases on the N-terminal and C-terminal sides of the fragment containing the functional domain of epimorphin, respectively, are separately prepared by DNA synthesizer. A double-stranded DNA encoding the intended modified epimorphin is then obtained by PCR making use of the cDNA (A) as a template, and the DNAs (B) and (C) as primers. After the thus-obtained DNA is integrated into a proper site of an expression vector, gene transfer is performed into a proper host such as *Escherichia coli* or animal cells. The gene-transferred host is cultured under suitable conditions to induce the expression of the transgene, thereby preparing the modified epimorphin.

Since the modified epimorphin according to the present invention has a nature that it is easily dissolved in a physiological solution, its mass production and purification can be performed with ease. In addition, such a modified epimorphin keeps the high epimorphin activity. The thus-obtained modified epimorphin is purified by an appropriate method, for example, affinity chromatography or the like, and then used as it is. When a plurality of modified epimorphin molecules is chemically crosslinked to each other to form a complex, however, higher activity may be exhibited in some cases. In this case, the crosslinking may be conducted with ease by an irradiation treatment with ultraviolet (UV) rays or a chemical modification making use of a chemical substance such as glutaraldehyde or DSS (disuccinimidyl suberate). These crosslinking treatments may make the solubility of the resulting complex in physiological solutions lowered. For example, when the modified epimorphin is coated on a base material such as a plastic or metal to use, it is therefore necessary to give such considerations that the crosslinking treatment is performed after the coating of the modified epimorphin.

For example, the counting of the number of attached cells and the reactivity with the monoclonal antibody MC-1 may be used as indices to the evaluation of activity of the modified epimorphin. As examples of the method of counting the number of attached cells, may be mentioned the following methods. The modified epimorphin is suspended in a 8 M urea/Lysis buffer, and this suspension is coated on a suspension culture dish and then dried. Thereafter, the thus-coated dish is washed once with the 8 M urea/Lysis buffer and then 5 times with PBS. Cultured cells CH3/10T1/2 clone 8 (product of Dainippon Pharmaceutical Co., Ltd.) suspended in a D-MEM/F-12 medium (SIGMA D8900) added with 20 mg/ml of BSA (Bovine Serum, Albumin) were then seeded on the coated dish. After being left over for a predetermined period of time (for example, 4 hours), the dish is washed 3 times with PBS, and the cells are then lysed with 0.5 N NaOH, followed by recovery of the resultant solution to measure the amount of DNA by a spectrophotometer, thereby counting the number of cells attached to the dish. Alternatively, an untreated polystyrene surface is coated with the modified epimorphin (10 $\mu$/cm$^2$), and thoroughly washed with PBS. Thereafter, MDCKII cells (model of epithelial cells) suspended in a serum-free medium (Dulbecco MEM) containing 20 mg/ml of BSA are seeded on the surface. After being left over for a predetermined period of time (for example, 8 hours), the number of cells attached to the surface is determined. These methods can also be applied to epimorphin and fragments of epimorphin.

As an index to the evaluation of solubility of the modified epimorphin, there may be used the amount of a fraction soluble in a physiological solution such as PBS. More specifically, the solubility may be evaluated by an amount of a soluble fraction when 1 mg of a protein is dissolved in 1 ml of PBS at 37° C. Therefore, the fact that 85% of the protein is soluble means that 0.85 mg of the protein is dissolved when 1 ml of PBS is added to 1 mg of the protein to mix them.

Modified Epimorphin Composed of a Polypeptide Having a Structure that at Least Part of Amino Acids Have Been Deleted From the Terminal Side of at Least One of the Coiled Coil Domains (1) and (3)

The central fragment (2) of epimorphin is a functional domain of epimorphin. Fragments containing the functional domain (2) are expected to apply to various uses making good use of the epimorphin activity thereof. However, the polypeptides containing the functional domain (2) may be insoluble or hardly soluble in physiological solutions, or low in activity. When the C-terminal hydrophobic domain is deleted from the whole-length epimorphin, a polypeptide soluble in the physiological solutions can be obtained. However, such a polypeptide is low in activity.

As a result of a detailed analysis as to the activity and solubility of the fragments of epimorphin, it has been found that the fragment (123) is soluble, but extremely low in activity, and the fragment (23) is insoluble, but high in activity by contrast. From this, the present inventors after the following hypothesis as to the work of the fragment (1). Namely, the fragment (1) negatively works on activity due to the action in masking the functional domain, but works on the solubility to enhance it owing to its action in changing to change the high-order structure of the fragment (23).

Figure 6:
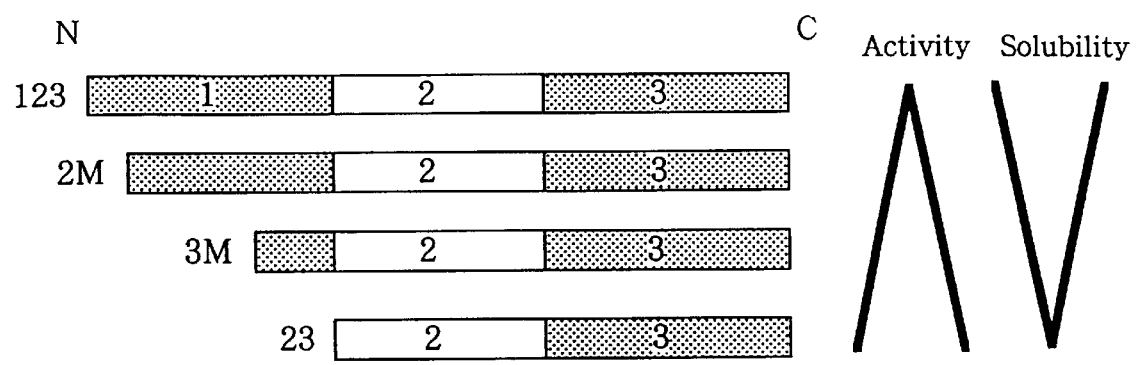
FIG. 6 illustrating a relationship between activity and solubility of epimorphin fragments.

Thus, the present inventors have produced a 2M fragment obtained by deleting 28 amino acids (in the case of human epimorphin) or 29 amino acids (in the case of mouse epimorphin) from the N-terminal side of the fragment (123), a 3M fragment obtained by deleting 77 amino acids (in the case of human epimorphin) or 78 amino acids (in the case of mouse epimorphin) from the N-terminal side of the fragment (123), and a fragment (23) as illustrated in FIG. 6 to analyze their properties. As a result, it has been revealed that the epimorphin fragments have a relationship that the activity increases, but on the other hand, the solubility decreases as the number of amino acids deleted from the N-terminal side is increased as illustrated in FIG. 6 (see the right of the drawing). It has thus been revealed that the activity and solubility of epimorphin polypeptides can be controlled by increasing or decreasing the number of amino acids to be deleted from the N-terminal side.

According to the present invention, as described above, there are provided modified epimorphin polypeptides, the activity and solubility of which can be controlled for the purpose of developing diagnosis and medical treatment for diseases caused by the morphogenetic abnormality of epithelial tissue, or novel remedies for wounds and the like.

More specifically, in the case where one attaches much importance to the activity, it is only necessary to produce a fragment with the number of amino acids deleted from the N-terminal side increased. In the case of human epimorphin, it is only necessary to produce a polypeptide having a structure wherein at least part of the amino acid(s) have been deleted in a range of from 78 to 103 amino acids, preferably, from 91 to 103 amino acids from the N-terminal side in order to obtain a modified epimorphin high in activity. In the case of mouse epimorphin, it is only necessary to produce a polypeptide having a structure wherein at least part of the amino acid(s) have been deleted in a range of from 79 to 104 amino acids, preferably, from 92 to 104 amino acids from the N-terminal side in order to obtain a modified epimorphin high in activity. For example, the fragment (23) may preferably be used.

In the case where one attaches much importance to the solubility, it is only necessary to produce a fragment with the number of amino acids deleted from the N-terminal side decreased. In the case of human epimorphin, it is only necessary to produce a polypeptide having a structure wherein at least part of the amino acid(s) have been deleted in a range of from 1 to 28 amino acids, preferably, from 14 to 28 amino acids from the N-terminal side in order to obtain a modified epimorphin high in solubility. In the case of mouse epimorphin, it is only necessary to produce a polypeptide having a structure wherein at least part of the amino acid(s) have been deleted in a range of from 1 to 29 amino acids, preferably, from 14 to 29 amino acids from the N-terminal side in order to obtain a modified epimorphin high in activity. For example, the fragment (2M) may preferably be used.

In the case where a fragment well balanced between the activity and the solubility is intended to be used, it is only necessary to produce a fragment in which the number of amino acid deleted from the N-terminal side is intermediate between the above ranges. In the case of human epimorphin, it is only necessary to produce a polypeptide having a structure wherein at least part of the amino acid(s) have been deleted in a range of from 29 to 77 amino acids, preferably, from 61 to 77 amino acids from the N-terminal side. In the case of mouse epimorphin, it is only necessary to produce a polypeptide having a structure wherein at least part of the amino acid(s) have been deleted in a range of from 30 to 78 amino acids, preferably, from 62 to 78 amino acids been deleted from the N-terminal side. For example, the fragment (3M) may preferably be used.

As described above, the modified epimorphin according to the present may be used properly with its structure changed according to the purpose and application intended. Therefore, the use of the modified epimorphin according to the present invention allows for the development of diagnosis and medical treatment for diseases caused by the morphogenetic abnormality of epithelial tissue, or the development of novel remedies for wounds and the like to more effectively progress. Epimorphin is a protein composed of about 280 amino acids. The mouse epimorphin is useful in, for example, elucidating the attack mechanism of diseases caused by the morphogenetic abnormality of the epithelial tissue making use of model animals. The human epimorphin is useful in, for example, diagnosing and treating such diseases. These molecules exist in mesenchymal cells around the epithelial tissue and have a function of controlling the morphogenesis of the epithelial tissue, and the like.

As a method of deleting amino acids from the N-terminal side of epimorphin, there may be used various techniques such as biochemical techniques and gene engineering techniques. As an example of a method making use of a biochemical technique, may be mentioned a process in which an epimorphin molecule is chemically or physically cleaved to obtain the above-described fragments. As an example of a method making use of a gene engineering technique, may be mentioned a process in which cDNA encoding each of the fragments of epimorphin is integrated into an appropriate vector to express the fragment in a host. As a specific technique, there may be used, for example, the following simple technique.

cDNA (A) encoding the whole-length epimorphin is first synthesized by polymerase chain reaction (PCR). On the other hand, single-stranded DNAs (B and C), in which 10 to 20 bases on the N-terminal and C-terminal sides of the epimorphin fragment to be prepared are joined to one another, respectively, are separately prepared by a DNA synthesizer. A double-stranded DNA encoding the intended modified epimorphin is then obtained by PCR making use of the cDNA (A) as a template, and the DNAs (B) and (C) as primers.

The thus-obtained double-stranded DNA is integrated into a vector having a structure capable of expressing the DNA, for example, pET3C (RIKEN DNA Bank RDB519) to prepare a recombinant vector. This recombinant vector is then introduced into a proper host, for example, BL21 (RIKEN DNA Bank RDB022) to obtain a transformant. After propagating this transformant in a large amount, a treatment for inducing expression, for example, the addition of IPTG to a medium so as to give a final concentration of 1 mM, is given to obtain the intended modified epimorphin.

DNA sequences encoding the fragments (2M), (3M), (23) and (123) of the human epimorphin are shown in the SEQUENCE Listing. SEQ ID NOs. 7, 8, 9 and 10 are DNA sequences of the fragments (2M), (3M), (23) and (123) of the human epimorphin, respectively.

In the SEQUENCE Listing, are shown DNA sequences encoding the fragments (2M), (3M), (23) and (123) of the mouse epimorphin. SEQ ID NOs. 11, 12, 13 and 14 are DNA sequences of the fragments (2M), (3M), (23) and (123) of the mouse epimorphin, respectively.

Amino acid sequences of the fragments (2M), (3M) and (23) of the human epimorphin are shown in the SEQUENCE Listing. SEQ ID NOs. 15, 16 and 17 are amino acid sequences of the fragments (2M), (3M) and (23) of the human epimorphin, respectively.

Amino acid sequences of the fragments (2M), (3M) and (23) of the mouse epimorphin are shown in the SEQUENCE Listings. SEQ ID NOs. 18, 19 and 20 are amino acid sequences of the fragments (2M), (3M) and (23) of the mouse epimorphin, respectively.

The modified epimorphin according to the present invention keeps the activity inherent in epimorphin at a high level, and is hence used directly in various applications including medical care, for example, treatments of various tissues for burns or scalds, or after surgery, and artificial organs. Besides, it may also be used at a low concentration as a component for cosmetics, hair growth stimulants and the like as it is.

The modified epimorphin according to the present invention may be a variant obtained by making partial substitution, deletion and/or insertion of amino acids in the amino acid sequence of the modified epimorphin so far as it substantially keeps the epimorphin activity. The partial substitution, deletion and insertion of amino acids may be made either singly or in any combination thereof. The site of the amino acid sequence (the variable site), at which the partial substitution, deletion or insertion of amino acids is made, is generally in the amino acid sequence of a polypeptide containing the functional domain (2) of epimorphin. This variable site may be in the amino acid sequence of the functional domain (2) of epimorphin. Such a variant itself may be easily produced by the method known per se in the art. Namely, the technique itself, in which partial substitution, deletion or insertion is made in the amino acid sequence of a protein to obtain a variant of the protein, is generally known. For example, recombinant PCR ("PCR Protocols" 155–160, Harcourt Brace Javanovich Japan Inc. 1991) or producing method of recombinant gene with PCR ("Experimental Medicine" Vol. 8, No. 9, 63–67, Yodosha Co., Ltd. 1990). The variant modified epimorphin according to the present invention may preferably substantially keep the functions inherent in the modified epimorphin, such as good cellular adhesiveness.

ADVANTAGES OF THE INVENTION

According to the present invention, the modified epimorphin which keeps the high activity of epimorphin and are easy to prepare and purify is provided by adding a hydrophilic peptide to a polypeptide containing the functional domain (2) of epimorphin. Besides, according to the present invention, the modified epimorphin, which is excellent in both activity and solubility, is provided by deleting at least part of amino acids from the terminal side of at least one of the coiled coil domains (1) and (3). More specifically, the modified epimorphin which is soluble and excellent in activity, or the modified epimorphin which is active and excellent in solubility, is provided. According to the present invention, there are further provided variants obtained by making partial substitution, deletion and/or insertion of amino acids in the amino acid sequence of the modified epimorphin. The modified epimorphin and variants thereof according to the present invention are soluble in physiological solutions and can hence be mass-produced and are easy to purify. The modified epimorphin and variants thereof of this invention keep the activity inherent in epimorphin at a high level, and may be used directly in various applications including medical care, for example, treatments of various tissues for burns or scalds, or after surgery, and artificial organs. Besides, they are useful as a component for cosmetics, hair growth stimulants and the like.

The proper use of the modified epimorphin and variants thereof according to the intended application in the research and medical fields allows the development of diagnosis and medical treatment for diseases caused by the morphogenetic abnormality of epithelial tissue, or the development of novel remedies for wounds and the like to more effectively progress.

EMBODIMENTS OF THE INVENTION

The present invention will hereinafter be described in more detail by the following examples.

REFERENTIAL EXAMPLE 1

The analysis by a computer revealed that the constitutive amino acids of epimorphin are divided into four structurally-characteristic domains as illustrated in FIG. 1. Incidentally, the coiled coil domains (1) and (3) can each be further divided into four subfragments.

Thus, with respect to mouse epimorphin (polypeptide composed of 289 amino acids in the whole length) represented by SEQ ID NO.4 of the SEQUENCE Listing, peptide fragments corresponding to the respective domains were first designed as illustrated in FIG. 1 (fragments indicated by 1, 2, 3, 12, 13, 23, 123 and 123C at lower rows in FIG. 1).

Figure 2:
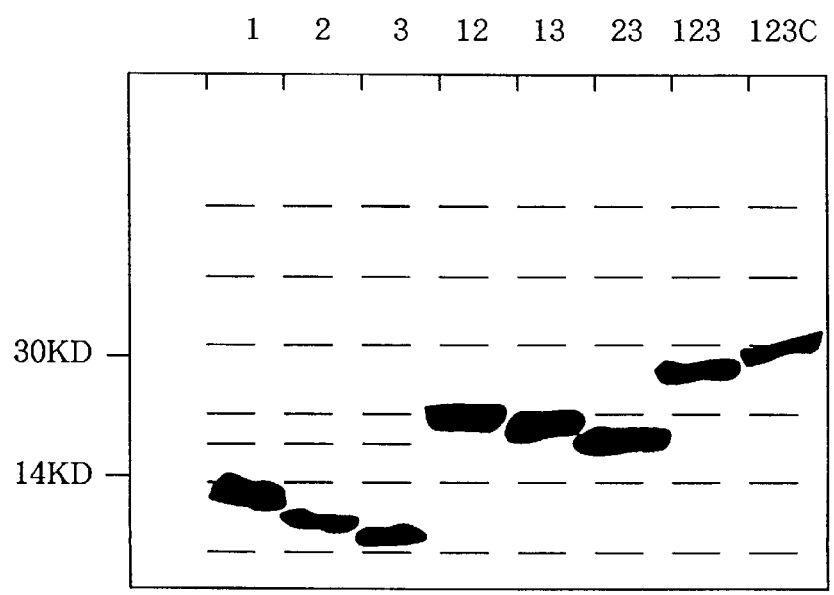
FIG. 2 is an electrophoretogram obtained by preparing the fragments shown in FIG. 1 using *Escherichia coli* and analyzing them by SDS-PAGE.
Figure 3:
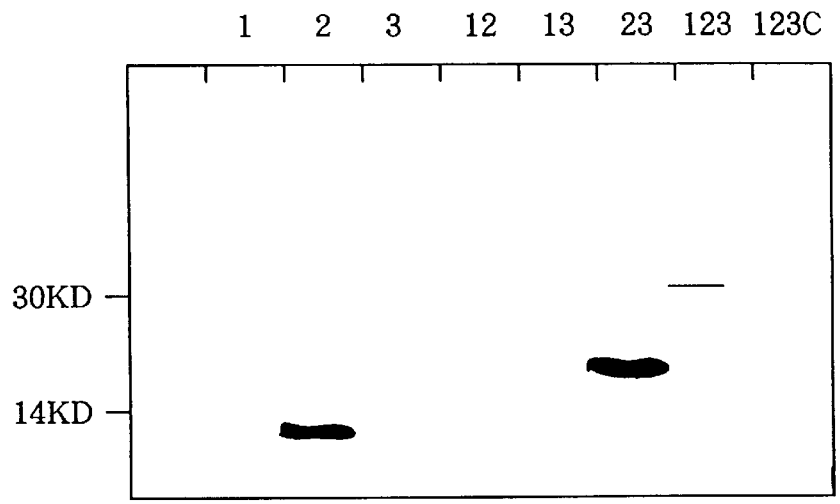
FIG. 3 illustrates a result that functional epimorphin fragments has been detected from the fragments shown in FIG. 2 using an antibody binding to the functional site of epimorphin.

Respective cDNAs encoding the peptide fragments were separately prepared by PCR making use of the whole-length cDNA of the mouse epimorphin as a template, and separately inserted into the NdeI-BamH1 site of an expression vector PET3C [Gene, Vol. 56, 125–135 (1987)]. The thus-obtained vector/fragment cDNAs were separately introduced into Escherichia coli to induce them with IPTG (1 mM, 2 hours), thereby producing the respective epimorphin fragments in the Escherichia coli. Total proteins in the Escherichia coli were analyzed by SDS-PAGE. As a result, it was found that all the epimorphin fragments were produced in substantially equal amounts (see FIG. 2). These fragments were then electrically transferred to a nitrocellulose membrane to determine the functional site of epimorphin with a monoclonal antibody MC-1 [Cell, Vol. 69, 471–481 (1992)] which binds to the functional site. The domain situated at the center of the epimorphin molecule was found to correspond to the functional site (see FIG. 3).

Even in the fragments containing the functional domain, those containing a sequence on the N-terminal side or a hydrophobic domain composed of 23 to 24 amino acids adjacent to the C-terminus at the same time were found to be low in the reactivity to the antibody (namely, the functional site was masked). Therefore, the function was not smoothly exhibited (compare the fragments 12 and 123 with the fragment 2 and 123C in FIG. 3, respectively). The fragment indicated by 23 in FIG. 3 was extracted from the Escherichia coli to purify it. As a result, it was revealed that when amino acids up to 99th amino acid from the C-terminus are deleted from such a fragment, the solubility of epimorphin in a physiological solution (PBS) is significantly increased (the insolubility of at least 95% turned to the solubility of 40%). Namely, the fragment 23 has limited solubility compared with the fragment 2. However, its solubility is increased by deleting the fragment 3.

On the basis of the results thus obtained, it was found that it is only necessary to contain an amino acid sequence ranging from the 100th amino acid to the 190th amino acid from the N-terminus in order to exhibit the function of epimorphin, that its function is gradually improved by successively deleting 30 to 99 amino acids from the N-terminal side, and that its solubility is gradually improved by successively deleting 25 to 99 amino acids from the C-terminal side.

EXAMPLE 1

A cDNA encoding a fragment (amino acid sequence ranging from 100th to 190th amino acids from the N-terminus) containing the functional domain of mouse epimorphin was prepared by PCR in the same manner as in Referential Example 1 and inserted into the NdeI or BamH1 site of a vector PET3C [Gene, Vol. 56, 125–135 (1987)]. The thus-obtained vector/fragment cDNA was then introduced into Escherichia coli to produce polypeptides in which a peptide ASMTGGQQMGR (SEQ ID NO. 26) was added as a hydrophilic peptide to the C-terminus or N-terminus of the above fragment.

The thus-obtained polypeptides were purified. As a result, all the polypeptides had a solubility of about 50% (namely, the solubility was improved by 10%). Even in the cases where peptides YPYDVPDYA, (SEQ ID NO. 21) EQKLISEEDLN, (SEQ ID NO. 22) EYKEEEEK, (SEQ ID NO. 23) YTDIEMNRLGK, (SEQ ID NO. 24) RIQRGPGRAFVTIGK, (SEQ ID NO. 25) QPELAPEDPED (SEQ ID NO. 27) and GAPVPYDPLEPR (SEQ ID NO. 28) were separately added in accordance with the same procedure as described above, the solubility was recognized to be improved by about 5–15%. The polypeptides thus obtained were all able to be detected with good reproducibility by commercially-available specific antibodies.

On the other hand, a cDNA produced by selecting, as one of primers, a product obtained by connecting a single-stranded DNA encoding the sequence (ASMTGGQQMGR) (SEQ ID NO. 26) composed of 11 amino acids to a positive-chain DNA encoding an amino acid sequence ranging from the 100th to 115th amino acids of epimorphin was inserted into the NdeI site of the above vector to conduct the same procedure as described above, thereby producing polypeptides in which the eleven amino acids were added to both C-terminus and N-terminus of the epimorphin functional domain-containing fragment. The thus-obtained polypeptides had a solubility of at least 85% in PBS.

MDCKII cells (model of epithelial cells) were suspended in a medium (Dulbecco MEM added with 10% serum) and then incubated for 8 hours in the presence of an equiamount of the soluble fraction of the epimorphin fragment. The thus-incubated cells were washed and then electrophoresed to detect the epimorphin fragments bound to the cells using an anti-ASMTGGQQMGR (SEQ ID NO.26) antibody (anti-T7-tag monoclonal antibody, product of Nobagen Co.). As a result, it was revealed that the epimorphin functional domain-containing fragment (modified epimorphin fragment) to both C-terminus and N-terminus of which the hydrophilic peptides composed of the eleven amino acids were added particularly firmly bound to the cells and then incorporated therein.

EXAMPLE 2

A single-stranded DNA (99 bases) encoding the 11 amino acid sequence (ASMTGGQQMGR) (SEQ ID NO. 26) repeatedly 3 times was produced by a DNA synthesizer and then converted to a double-stranded DNA with DNA polymerase. This DNA was inserted repeatedly several times into PET3C vectors in which DNAs respectively encoding the epimorphin functional domain-containing fragments obtained in Example 1, to the C-terminus or N-terminus of which the amino acids had been added, had been separately inserted, thereby producing epimorphin functional domain-containing fragments, to both C-terminus and N-terminus of which amino acids of various lengths (11, 33, 66, 99, 44, 76 and 110) were added. *Escherichia coli.*

The function of the fragments thus obtained was evaluated with the MDCKII cells in the same manner as in Example 1. As a result, it was found that good cellular adhesiveness is recognized in the cases where the amino acids are added up to the number of 99 to both N- and C-termini, but the cellular adhesiveness tends to lower when the length of the amino acids added becomes longer than 99.

EXAMPLE 3

Polypeptides in which 3 to 15 consecutive His residues were added to the N-terminus of a fragment composed of the functional domain (amino acid sequence ranging from the 105th to 188th amino acids from the N-terminus) of mouse epimorphin were first produced in *Escherichia coli* in the same manner as in Example 1. The *Escherichia coli* strain thus obtained was lysed in 8 M urea to attempt one-step purification through a Ni-agarose column. As a result, it was possible to purify fragments which did not contain any other contaminant when a hydrophilic peptide containing at least 5 consecutive His residues was added.

EXAMPLE 4

Figure 4:
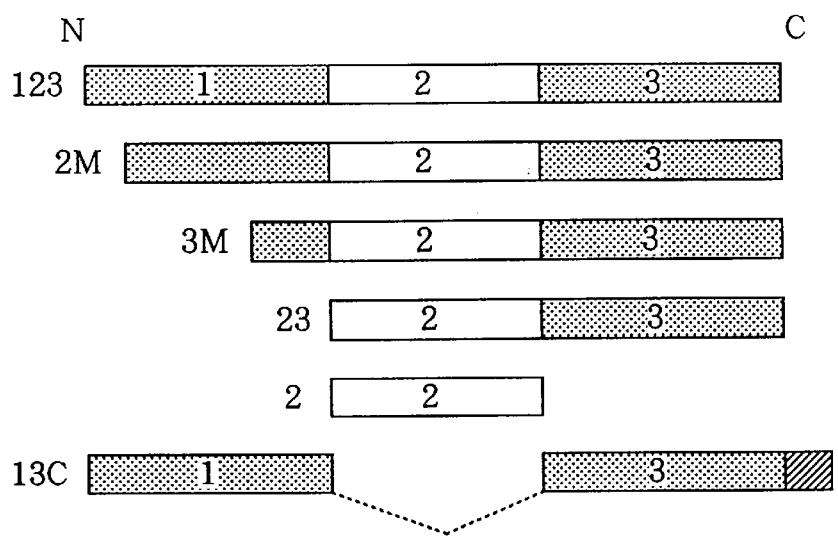
FIG. 4 illustrates the design drawing of epimorphin fragments used in Example 4.

Polypeptides in which 6 consecutive His residues were added to the N-termini of epimorphin fragments of various lengths containing the functional domain of mouse epimorphin were first produced in the same manner as in Example 1. The respective fragments are shown in FIG. 4. In FIG. 4, the fragments are as follows:

123: a fragment ranging from the N-terminus to right before the C-terminal hydrophobic domain;

2M: a fragment ranging from the 30th amino acid from the N-terminus to right before the C-terminal hydrophobic domain;

3M: a fragment ranging from the 79th amino acid from the N-terminus to right before the C-terminal hydrophobic domain;

23: a fragment ranging from the 105th amino acid from the N-terminus to right before the C-terminal hydrophobic domain;

2: a fragment ranging from the 105th amino acid to the 188th amino acid from the N-terminus; and 13C: a fragment obtained by deleting the fragment 2 from the whole-length epimorphin.

These fragments were then purified through a Ni-agarose column and separately coated on culture dishes, and angioendothelial cells were then seeded on the dishes. As a result, the angioendothelial cells rapidly adhered to all the peptides containing the functional domain (the fragment 2). However, no cell adhesion was observed on the fragment obtained by deleting only the functional domain from the whole-length epimorphin.

The amounts of factors secreted by the cells adhered were determined. As a result, it was found that the fragment obtained by adding the His residues to the fragment 123 is highest in activity.

EXAMPLE 5

An internal ear of a rabbit was first wounded in a size 6 mm across and 1 mm deep by a punch. This wound was treated with 1–10 μg of the modified epimorphin fragment (peptide containing the fragment 123) obtained in Example 4 and then taped. After 1 week, the tape was taken out of the wounded site to prepare slices from this wounded site, thereby determining reepithelialization rate, granulation rate and the number of neoplastic vessels. As a result, this modified epimorphin fragment was found to be useful in healing wounds. The use of the modified epimorphin fragment (peptide containing the fragment 3M) obtained in Example 4 gave the same results as described above. Therefore, it is understood that the modified epimorphin fragments containing the functional domain are useful in healing wounds.

EXAMPLE 6

The modified epimorphin fragment produced in Example 1, in which the hydrophilic peptide composed of the eleven amino acids (ASMTGGQQMGR) (SEQ ID NO. 26) had been added to both termini thereof, was coated on two positions of an untreated polystyrene surface in density of 10 μg/cm$^2$. One of the coated portions was crosslinked with DSS (disuccinimidyl suberate). After the thus-coated surface was thoroughly washed with PBS, MDCKII cells suspended in a serum-free medium (Dulbecco MEM) containing 20 mg/ml of BSA were seeded on the surface. After 2 hours and 8 hours, the number of cells attached to the fragments was determined. As a result, it was revealed that MDCKII rapidly and strongly bind to the crosslinked portion (see Table 1). Incidentally, the coating fragments on the polystyrene surface were dissolved in a sample buffer containing SDS without seeding the cells to collect them, thereby analyzing them by electrophoresis. As a result, it was confirmed that only the fragment subjected to the DSS treatment was polymerized.

TABLE 1

|  | Modified epimorphin obtained by adding the hydrophilic peptide composed of 11 amino acids to both termini of the epimorphin functional domain-containing fragment | Modified epimorphin obtained by adding the hydrophilic peptide composed of 11 amino acids to both termini of the epimorphin functional domain-containing fragment and crosslinking with DSS |
| --- | --- | --- |
| Number of cells attached after 2 hours | 10% | 70% |
| Number of cells attached after 8 hours | 85% | 90% |

(Note)
The number of attached cells (%) is a value calculated out on the basis of the whole number (100%) of cells seeded.

EXAMPLE 7

Production of Modified Epimorphin (1) Cell

A mesenchymal cell strain expressing epimorphin, for example, CH3/10T1/2 clone 8 (Code No. 08-226, product of Dainippon Pharmaceutical Co., Ltd.) was purchased to culture it in accordance with the description thereof.

(2) Preparation of RNA

A TRIzol Reagent (Cat. No. 15596-026) produced by Lifetec Oriental K.K. was used in the preparation of RNA. The RNA was prepared in accordance with a protocol attached to the product.

After the preparation, the RNA was treated with DNase I (Cat. No. 8068SA, amplification grade) produced by Lifetec Oriental K.K. in accordance with a protocol attached to the product.

(3) Preparation of Epimorphin cDNA by RT-PCR

On the basis of the RNA thus prepared, a reverse transcription was performed with an RNA PCR kit (Cat. No. RO12) available from Takara Shuzo Co., Ltd. in accordance with a protocol attached to the product.

In order to amplify only cDNA of epimorphin, both upstream primer and downstream primer (5'ATGCGGGACCGGCTG3' (SEQ ID NO. 29) and 5'TCATTTGCCAACCGA3' (SEQ ID NO. 30)) specific for epimorphin were then used to perform PCR in accordance with a protocol attached to the product, thereby obtain epimorphin cDNA. The preparation of the upstream and downstream primers specific for epimorphin was entrusted to Bex K.K.

(4) Preparation of Fragments

With respect to cDNAs encoding the fragments (2M), (3M), (23) and (123) of human epimorphin, base sequences of primers specific for the respective fragments were determined from SEQ ID NO. 7 (human 2M), SEQ ID NO. 8 (human 3M), SEQ ID NO. 9 (human 23), SEQ ID NO. 10 (human 123), and primers with a restriction enzyme NdeI site (5'CATATG3') and a restriction enzyme NheI site (5'GCTAGC3') tagged on the 5' side of the upstream primer and the 5' side of the downstream primer, respectively, were purchased from Bex K.K.

Similarly, with respect to cDNAs encoding the fragments (2M), (3M), (23) and (123) of mouse epimorphin, base sequences of primers specific for the respective fragments were determined from SEQ ID NO. 11 (mouse 2M), SEQ ID NO. 12 (mouse 3M), SEQ ID NO. 13 (mouse 23), SEQ ID NO. 14 (mouse 123), and primers with a restriction enzyme NdeI site (5'CATATG3') and a restriction enzyme NheI site (5'GCTAGC3') tagged on the 5' side of the upstream primer and the 5' side of the downstream primer, respectively, were purchased from Bex K.K.

The respective fragments were obtained by PCR making use of respective pairs of the primers. The PCR was performed with a Takara Taq (Cat. No. R001A) available from Takara Shuzo Co., Ltd. in accordance with a protocol attached to the product.

(5) Subcloning

Each of the double-stranded DNAs thus obtained was integrated into an expression vector, for example, a vector derived from ET3C (RIKEN DNA Bank RDB519) by deleting a domain lying between two EcoRV sites thereof, in accordance with the process de scribed in "Laboratory-Manual Gene Engineering", 111–114 (1988), published by Maruzen Co., Ltd., thereby producing a recombinant vector.

This recombinant vector was then introduced into a host, BL21 (RIKEN DNA Bank RDB022), in accordance with the Hanahan method described in "Laboratory-Manual Gene Engineering", 108–109, thereby obtaining transformants.

(6) Screening

Colonies grown on an LB plate (1% Bacto-tryptone, 0.5% Bacto-yeast extract, 1% NaCl, 1.5% Bacto-agar) containing 50 μg/ml of ampicillin were selected to conduct the primary screening of the transformants.

In order to finally identify the transformants having the recombinant vector, the recombinant vector contained in the transformant was used as a template to perform PCR using the upstream and downstream primers specific for the modified epimorphin intended to ascertain whether the epimorphin cDNAs were present or not (at this point of time, 9 clones out of 10 clones contained the cDNAs).

After the transformants thus obtained were propagated in large amounts by shaking culture at 37° C. on a liquid LB medium (1% Bacto-tryptone, 0.5% Bacto-yeast extract, 1% NaCl) containing 50 μg/ml of ampicillin, a substance, IPTG, for inducing expression was added to the medium so as to give a final concentration of 1 mM. Thereafter, the shaking culture was continued for 2 hours at 37° C., thereby producing various human and mouse modified epimorphin polypeptides in *Escherichia coli*.

Total proteins in the *Escherichia coli* strain were analyzed by SDS-PAGE. As a result, it was found that all the modified epimorphin fragments were produced in substantially equal amounts.

EXAMPLE 8

Investigation as to Solubility of the Respective Modified Epimorphin Polypeptides Each of the transformants prepared in Example 7, which separately expressed the human and mouse modified epimorphin polypeptides, was suspended in a Lysis buffer [50 mM Tris-HCl (pH: 8.0), 1 mM EDTA, 100 mM NaCl] to wash it. The thus-washed transformant was subjected to centrifugation to precipitate the bacteria. After the thus-precipitated bacteria were suspended in a Lysis buffer, lysozyme (SIGMA L-6876) was added to the suspension to give a concentration of 1 mg/ml. The mixture was frozen and thawed repeatedly three times to lyse the *Escherichia coli* strain, followed by its ultrasonic treatment.

Thereafter, the supernatant was removed by centrifugation, and the resultant precipitate was washed 4 times with a 2 M urea/Lysis buffer. The thus-washed precipitate was suspended again in a 8 M urea/Lysis buffer, followed by centrifugation to obtain a supernatant fraction.

The thus-obtained supernatant fraction was dialyzed against an excess amount of a PBS buffer and further centrifuged, thereby separating it into a supernatant fraction and a precipitate fraction. The thus-obtained fractions were analyzed by SDS-PAGE to determine the solubility of each modified epimorphin by the proportions of the modified epimorphin existing in the respective fractions.

As a result, as illustrated in FIG. 6, there was shown a tendency for the modified epimorphin polypeptide to become more insoluble as the number of amino acids deleted from the N-terminal side thereof was increased.

EXAMPLE 9

Investigation as to Activity of the Respective Modified Epimorphin Polypeptides

As an index to the activity evaluation of the respective modified epimorphin polypeptides, their binding ability to cultured cells was investigated.

The modified epimorphin polypeptides (suspensions in 8 M urea/Lysis buffer) prepared in Example 8 were separately coated on suspension culture dishes and then dried. Thereafter, the thus-coated dishes were washed once with 8 M urea/Lysis buffer and then 5 times with PBS. Cultured cells CH3/10T1/2 clone 8 (product of Dainippon Pharmaceutical Co., Ltd.) suspended in a D-MEM/F-12 medium (SIGMA D8900) added with 20 mg/ml of BSA (SIGMA-A-7030) were then seeded on the coated dishes.

After being left over for 1 hour and one day, the dishes were washed 3 times with PBS, and the cells were then lysed with 0.5 N NaOH. The resultant solutions were then recovered and further centrifuged. Thereafter, the amount of DNA in each of the solutions was measured by a spectrophotometer, thereby counting the number of cells attached to the dish to use this value as an index to the activity evaluation of the respective modified epimorphin polypeptides. As illustrated in FIG. 6, the results showed a tendency for the degree of activity to become opposite to the solubility.

EXAMPLE 10

Preparation of Variant Modified Epimorphin (A): cDNA encoding the fragment (2) of mouse epimorphin.

(B): Single-stranded DNA obtained by binding a base sequence capable of recognizing a restriction enzyme NdeI to the 5'-terminus of single-stranded DNA composed of 10 to 20 bases from the 5'-terminal side of a sense strand of (A).

(C): Single-stranded DNA obtained by binding a base sequence capable of recognizing a restriction enzyme NheI to the 5'-terminus of single-stranded DNA composed of 10 to 20 bases from the 5'-terminal side of an anti-sense strand of (A).

(1) (B) and (C) were produced by a DNA synthesizer.

(2) (A), and (B) and (C) were used as a template and primers, respectively, to obtain double-stranded DNA by a PCR process. At this time, the PCR was performed under conditions described in "Technique-a Journal of Methods in Cell and Molecular Biology", Vol. 1, No. 1, 11–15 (August, 1989). By this process, DNAs encoding appropriate variant epimorphin fragments (2), in which substitution, variation occurred in part of the base sequence of (A), were obtained.

(3) The DNAs thus obtained were inserted into the NdeI/NheI site of pET3C, which was obtained by a domain lying between two EcoRV sites thereof, thereby producing a recombinant vector. This recombinant vector was then introduced into a host, *Escherichia coli* strain BL21 in accordance with the Hanahan process.

(4) This *Escherichia coli* strain was seeded on an LB plate (1% Bacto-tryptone, 0.5% Bacto-yeast extract, 1% NaCl, 1.5% Bacto-agar) containing 50 µg/ml of ampicillin to culture it overnight at 37°C.

(5) In order to identify colonies grown as transformants having the recombinant vector, a usual PCR process was performed to amplify the DNAs encoding the variant modified epimorphin fragments intended. Thereafter, the DNAs were subjected to agarose gel electrophoresis, thereby confirming its bands.

(6) After the transformants thus obtained were propagated in large amounts by shaking the culture at 37° C. on liquid LB medium containing 50 µg/ml of ampicillin, substance, IPTG, for inducing expression was added to the medium so as to give a final concentration of 1 mM. Thereafter, shaking of the culture was continued for 2 hours, thereby producing various variant modified epimorphin fragments in *Escherichia coli*.

(7) The *Escherichia coli* strain of (6) was suspended in Lysis buffer to wash it. The thus-washed strain was subjected to centrifugation to precipitate the bacteria and remove the supernatant. After the thus-precipitated bacteria were recovered and suspended in Lysis buffer, lysozyme was added to the suspension to give a concentration of 1 mg/ml. The mixture was frozen and thawed repeatedly three times to lyse the *Escherichia coli* strain, followed by its ultrasonic treatment. Thereafter, the supernatant was removed by centrifugation, and the resultant precipitate was washed 4 times with 2 M urea/Lysis buffer. The thus-washed precipitate was suspended again in 8 M urea/Lysis buffer, followed by centrifugation to obtain a supernatant fraction.

EXAMPLE 11

Determination of Amino Acid Sequence of Variant Modified Epimorphin

Plasmid DNAs in the *Escherichia coli* of the colonies in (5) of Example 10 were prepared by the alkali process ["Laboratory-Manual Gene Engineering" 51–53 (1988), published by Maruzen Co., Ltd.] to analyze the base sequences of the DNAs encoding the variant modified epimorphin fragments by a DNA sequencer. Amino acid sequences encoded by these base sequences were determined to take them as amino acid sequences of their corresponding variant modified epimorphin fragments obtained in Example 10.

EXAMPLE 12

Evaluation of Variant Modified Epimorphin in Cell Culture (1) The variant modified epimorphin fragments (suspensions in 8 M urea/Lysis buffer) prepared in Example 10 were coated on suspension culture dishes to give a coating weight of 10 μg/cm², and then dried. Thereafter, the thus-coated dishes were washed once with 8 M urea/Lysis buffer and then 5 times with PBS. Cultured cells CH3/10T1/2 clone 8 suspended in a D-MEM/F-12 medium (SIGMA D8900) added with 20 mg/ml of BSA were then seeded on the coated dishes.

(2) After being left over for 1 hour, the dishes were washed 3 times with PBS, and the cells were then recovered with 0.5 N NaOH. The value of OD at 260 nm, by which the amount of DNA contained therein was reflected, was determined by a spectrophotometer. The absorbance of an invariant modified epimorphin fragment was 0.33±0.015. Among the variant modified epimorphin fragments obtained, six fragments had an absorbance within about this range. This revealed that variants, in which part of their amino acid sequences have been varied, are permissible in the modified epimorphin.

The varied sites of the variant modified epimorphin fragments, which was produced and evaluated in Examples 10–12, are as shown in Table 2.

TABLE 2

| Variant | Varied site (*1) | Original amino acid | Varied amino acid |
|---|---|---|---|
| a | 149th | Ile | Val |
|   | 175th | Ser | Pro |
| b | 175th | Ser | Thr |
| c | 115th | Ile | Val |
|   | 127th | Phe | Leu |
|   | 130th | Val | Ala |
|   | 131th | Met | Thr |
|   | 139th | Ile | Val |
|   | 154th | Glu | Val |
|   | 166th | Glu | Asp |
|   | 177th | Phe | Leu |
| d | 134th | Tyr | Phe |
|   | 171th | Ser | Gly |
|   | 178th | Ile | Thr |
|   | 179th | Ser | Pro |
|   | 180th | Asp | Gly |
| e | 133th | Glu | Val |
|   | 145th | Ser | Gly |
|   | 155th | Ile | Asn |
|   | 162th | Asp | Gly |
|   | 177th | Phe | Ser |
| f | 122th | Asp | Gly |
|   | 115th | Ile | Leu |
|   | 131th | Met | Val |
|   | 155th | Ile | Phe |

(*1) The number counted from the N-terminus of the whole-length mouse epimorphin.

What is claimed is:

1. A modified epimorphin comprising a hydrophilic peptide composed of from 5 to 99 amino acids fused to the N-terminus, C-terminus or both the N- and C-termini of a polypeptide containing a functional domain of epimorphin which is a fragment of epimorphin comprising the 99th to 189th amino acids from the N-terminus of human epimorphin whose amino acid sequence is set forth in SEQ ID NO:1, or the 100th or 190th amino acids from the N-terminus of mouse epimorphin whose amino acid sequence is set forth in SEQ ID NO:4, said function domain promoting cell adhesion.

2. The modified epimorphin according to claim 1, wherein the polypeptide containing the functional domain of epimorphin is the whole-length epimorphin.

3. The modified epimorphin according to claim 1, wherein the polypeptide containing the functional domain of epimorphin is a fragment which has a deletion of at least one amino acid from the whole-length epimorphin from the N- or C-terminus thereof.

4. The modified epimorphin according to claim 3, wherein the polypeptide containing the functional domain of epimorphin is a fragment which has a deletion of at least one amino acid in the coiled coil domain from the whole-length epimorphin from the N-terminal side thereof.

5. The modified epimorphin according to claim 4, wherein the hydrophilic peptide is fused to at least the N-terminus of the fragment.

6. The modified epimorphin according to claim 3, wherein the polypeptide containing the functional domain of epimorphin is a fragment which has a deletion of the C-terminal hydrophobic domain from the whole-length epimorphin.

7. The modified epimorphin according to claim 6, wherein the hydrophilic peptide is fused to at least the N-terminus of the fragment.

8. The modified epimorphin according to claim 3, wherein the polypeptide containing the functional domain of epimorphin is a hydrophobic fragment which has a deletion of the C-terminal hydrophobic domain from the whole-length epimorphin and further has a deletion of at least one amino acid in the coiled coil domain from the N-terminal side.

9. The modified epimorphin according to claim 8, wherein the hydrophilic peptide is fused to at least the N-terminus of the fragment.

10. The modified epimorphin according to claim 3, wherein the polypeptide containing the functional domain of epimorphin is a fragment which has a deletion of the C-terminal hydrophobic domain from the whole-length epimorphin and further has a deletion of at least one amino acid in the coiled coil domain from the C-terminal side.

11. The modified epimorphin according to claim 10, wherein the hydrophilic peptide is fused to at least the C-terminus of the fragment.

12. The modified epimorphin according to claim 3, wherein the polypeptide containing the functional domain of epimorphin is a fragment which has a deletion of the C-terminal hydrophobic domain from the whole-length epimorphin and further has a deletion of at least one amino acid in the coiled coil domain from the N-terminal side and at least one amino acid in the coiled coil domain from the C-terminal side.

13. The modified epimorphin according to claim 1, wherein the hydrophilic peptide contains hydrophilic amino acids in a proportion of at least 50% based on the number of amino acids.

14. The modified epimorphin according to claim 7, wherein the hydrophilic peptide contains at least one amino acid sequence selected from the group consisting of the following amino acid sequences (a) to (h):

(a) Tyr-Pro-Tyr-Asp-Val-Pro-Asp-Tyr-Ala(SEQ ID NO:21);

(b) Glu-Gln-Lys-Leu-Ile-Ser-Glu-Glu-Asp-Leu-Asn (SEQ ID NO:22);

(c) Glu-Tyr-Lys-Glu-Glu-Glu-Glu-Lys(SEQ ID NO:23);

(d) Tyr-Thr-Asp-Ile-Glu-Met-Asn-Arg-Leu-Gly-Lys (SEQ ID NO:24);

(e) Arg-Ile-Gln-Arg-Gly-Pro-Gly-Arg-Ala-Phe-Val-Thr-Ile-Gly-Lys(SEQ ID NO:25);

(f) Ala-Ser-Met-Thr-Gly-Gly-Gln-Gln-Met-Gly-Arg (SEQ ID NO:26);

(g) Gln-Pro-Glu-Leu-Ala-Pro-Glu-Asp-Pro-Glu-Asp (SEQ ID NO:27); and (h) Gly-Ala-Pro-Val-Pro-Tyr-Asp-Pro-Leu-Glu-Pro-Arg (SEQ ID NO:28).

15. The modified epimorphin according to claim 1, wherein the hydrophilic peptide contains at least 5 consecutive histidine residues.

16. The modified epimorphin according to claim 1, which has been subjected to intermolecular crosslinking to form a complex.

17. The modified epimorphin according to claim 1, wherein the epimorphin is human epimorphin.

18. The modified epimorphin according to claim 17, wherein the epimorphin has at least an amino acid sequence ranging from the 99th amino acid to the 189th amino acid from the N-terminus of the human epimorphin having SEQ ID NO:1.

19. The modified epimorphin according to claim 17, wherein the polypeptide containing the functional domain of epimorphin is a fragment which has a deletion of 1 to 28 contiguous amino acids in the coiled coil domain from the N-terminus of the whole-length human epimorphin and has a deletion of the C-terminal hydrophobic domain therefrom, wherein the deletion occurs from the N-terminus.

20. The modified epimorphin according to claim 17, wherein the polypeptide containing the functional domain of epimorphin is a fragment which has a deletion of 29 to 98 contiguous amino acids from the N-terminus of the whole-length human epimorphin, wherein the deletion occurs from the N-terminus.

21. The modified epimorphin according to claim 17, wherein the polypeptide containing the functional domain of epimorphin is a fragment which has a deletion of 29 to 77 contiguous amino acids in the coiled coil domain from the N-terminus of the whole-length human epimorphin and has a deletion of the C-terminal hydrophobic domain therefrom, wherein the deletion occurs from the N-terminus.

22. The modified epimorphin according to claim 17, wherein the polypeptide containing the functional domain of epimorphin is a fragment which has a deletion of 78 to 98 contiguous amino acids in the coiled coil domain from the N-terminus of the whole-length human epimorphin and has a deletion of the C-terminal hydrophobic domain therefrom, wherein the deletion occurs from the N-terminus.

23. The modified epimorphin according to claim 17, wherein the polypeptide containing the functional domain of epimorphin is a fragment which has a deletion of 30 to 98 contiguous amino acids in the coiled coil domain from the N-terminus of the whole-length human epimorphin and has a deletion of the C-terminal hydrophobic domain therefrom, wherein the deletion occurs from the N-terminus.

24. The modified epimorphin according to claim 1, wherein the epimorphin is mouse epimorphin.

25. The modified epimorphin according to claim 24, wherein the epimorphin has at least an amino acid sequence ranging from the 100th amino acid to the 190th amino acid from the N-terminus of the mouse epimorphin having SEQ ID NO:4.

26. The modified epimorphin according to claim 24, wherein the polypeptide containing the functional domain of epimorphin is a fragment which has a deletion of 1 to 29 contiguous amino acids in the coiled coil domain from the N-terminus of the whole-length mouse epimorphin and has a deletion of the C-terminal hydrophobic domain therefrom, wherein the deletion occurs from the N-terminus.

27. The modified epimorphin according to claim 24, wherein the polypeptide containing the functional domain of epimorphin is a fragment which has a deletion of 30 to 99 contiguous amino acids from the N-terminus of the whole-length mouse epimorphin, wherein the deletion occurs from the N-terminus.

28. The modified epimorphin according to claim 24, wherein the polypeptide containing the functional domain of epimorphin is a fragment which has a deletion of 30 to 78 contiguous amino acids in the coiled coil domain from the N-terminus of the whole-length mouse epimorphin and has a deletion of the C-terminal hydrophobic domain therefrom, wherein the deletion occurs from the N-terminus.

29. The modified epimorphin according to claim 24, wherein the polypeptide containing the functional domain of epimorphin is a fragment which has a deletion of 79 to 99 contiguous amino acids in the coiled coil domain from the N-terminus of the whole-length mouse epimorphin and has a deletion of the C-terminal hydrophobic domain therefrom, wherein the deletion occurs from the N-terminus.

30. The modified epimorphin according to claim 24, wherein the polypeptide containing the functional domain of epimorphin is a fragment which has a deletion of 30 to 99 contiguous amino acids in the coiled coil domain from the N-terminus of the whole-length mouse epimorphin and has a deletion of the C-terminal hydrophobic domain therefrom, wherein the deletion occurs from the N-terminus.

31. A modified epimorphin comprising a functional domain which is a fragment of epimorphin comprising the 99th to 189th amino acids from the N-terminus of human epimorphin whose amino acid sequence set forth in SEQ ID NO:1 or the 100th to 190th amino acids from the N-terminus of mouse epimorphin whose amino acid sequence set forth in SEQ ID NO:4 wherein said functional domain promotes cell adhesion.

32. The modified epimorphin according to claim 31, wherein the epimorphin is human epimorphin.

33. The modified epimorphin according to claim 32, which is composed of a polypeptide having a structure wherein 1 to 28 contiguous amino acids have been deleted from the N-terminus, wherein a deletion occurs from the N-terminus.

34. The modified epimorphin according to claim 32, which is composed of a polypeptide having a structure wherein 29 to 77 contiguous amino acids have been deleted from the N-terminus, wherein a deletion occurs from the N-terminus.

35. The modified epimorphin according to claim 32, which is composed of a polypeptide having a structure wherein 78 to 98 contiguous amino acids have been deleted form the N-terminus, wherein a deletion occurs from the N-terminus.

36. The modified epimorphin according to claim 32, which is a human modified epimorphin having any one of amino acid sequences of SEQ ID NOS:15 to 17.

37. The modified epimorphin according to claim 31, wherein the epimorphin is mouse epimorphin.

38. The modified epimorphin according to claim 37, which is composed of a polypeptide having a structure wherein 1 to 29 contiguous amino acids have been deleted from the N-terminus, wherein a deletion occurs from the N-terminus.

39. The modified epimorphin according to claim 37, which is composed of a polypeptide having a structure wherein 30 to 78 contiguous amino acids have been deleted from the N-terminus, wherein a deletion occurs from the N-terminus.

40. The modified epimorphin according to claim 37, which is composed of a polypeptide having a structure wherein 79 to 99 continuous amino acids have been deleted from the N-terminus, wherein a deletion occurs from the N-terminus.

41. The modified epimorphin according to claim 37, which is a mouse modified epimorphin having any one of amino acid sequences of SEQ ID NOS:18 to 20.

42. A DNA encoding a modified epimorphin comprising a hydrophilic peptide composed of from 5 to 99 amino acids fused to the N-terminus, C-terminus or both the N- and C-termini of a polypeptide containing a functional domain of epimorphin which is a fragment of epimorphin comprising the 99th to 189th amino acids from the N-terminus of human epimorphin whose amino acid sequence is set forth in SEQ ID NO:1, or the 100th or 190th amino acids from the N-terminus of mouse epimorphin whose amino acid sequence is set forth in SEQ ID NO:4, said function domain promoting cell adhesion.

43. A DNA encoding a modified epimorphin comprising a functional domain which is a fragment of epimorphin comprising the 99th to 189th amino acids from the N-terminus of human epimorphin whose amino acid sequence is set forth in SEQ ID NO:1, or the 100th to 190th amino acids from the N-terminus of mouse epimorphin whose amino acid sequence is set forth in SEQ ID NO:4, wherein said functional domain promotes cell adhesion.

44. The DNA according to claim 43, which is DNA encoding a human modified epimorphin having any one of SEQ ID NOS:7 to 9.

45. The DNA according to claim 43, which is DNA encoding a mouse modified epimorphin having any one of SEQ ID NOS:11 to 13.

46. A recombinant vector which contains DNA encoding a modified epimorphin comprising a hydrophilic peptide composed of from 5 to 99 amino acids fused to the N-terminus, C-terminus or both the N- and C-termini of a polypeptide containing a functional domain of epimorphin which is a fragment of epimorphin comprising the 99th to 189th amino acids from the N-terminus of human epimorphin whose amino acid sequence is set forth in SEQ ID NO:1, or the 100th or 190th amino acids from the N-terminus of mouse epimorphin whose amino acid sequence is set forth in SEQ ID NO:4, said function domain promoting cell adhesion.

47. A transformant obtained by introducing a recombinant vector according to claim 46 to a cell or microorganism which is capable of expressing the modified epimorphin.

48. The transformant according to claim 47, wherein a host of the transformant is *Escherichia coli*.

49. A recombinant vector which contains DNA encoding a modified epimorphin comprising a functional domain which is a fragment of epimorphin comprising the 99th to 189th amino acids from the N-terminus of human epimorphin whose amino acid sequence is set forth in SEQ ID NO: 1, or the 100th to 190th amino acids from the N-terminus of mouse epimorphin whose amino acid sequence is set forth in SEQ ID NO: 4, wherein said functional domain promotes cell adhesion.

50. The recombinant vector according to claim 49, which contains DNA encoding a human modified epimorphin having any one of SEQ ID NOS: 7 to 9.

51. The recombinant vector according to claim 49, which contains DNA encoding a mouse modified epimorphin having any one of SEQ ID NOS: 11 to 13.

52. A transformant obtained by introducing a recombinant vector according to claim 49 to a cell or microorganism which is capable of expressing the modified epimorphin.

53. The transformant according to claim 52, which is obtained by introducing a recombinant vector to a cell or microorganism, wherein said vector contains DNA encoding a human modified epimorphin having any one of SEQ ID NOS: 7 to 9.

54. The transformant according to claim 52, which is obtained by introducing a recombinant vector to a cell or microorganism, wherein said vector contains DNA encoding a mouse modified epimorphin having any one of SEQ ID NOS: 11 to 13.

55. The transformant according to claim 52, wherein a host of the transformant is *Escherichia coli*.

56. A method of producing a modified epimorphin, comprising the steps as follows:
culturing a transformant obtained by having a cell or microorganism introduced with a recombinant vector which contains DNA encoding a modified epimorphin comprising a hydrophilic peptide composed of from 5 to 99 amino acids fused to the N-terminus, C-terminus or both the N- and C-termini of a polypeptide containing a functional domain of epimorphin which is a fragment of epimorphin comprising the 99th to 189th amino acids from the N-terminus of human epimorphin whose amino acid sequence is set forth in SEQ ID NO:1, or the 100th or 190th amino acids from the N-terminus of mouse epimorphin whose amino acid sequence is set forth in SEQ ID NO:4, said function domain promoting cell adhesion;
adding IPTG to induce expression of the modified epimorphin;
recovering the transformant;
lysing the transformant; and
obtaining the modified epimorphin from the resultant lysate.

57. A method of producing a modified epimorphin, comprising the steps as follows:
culturing a transformant obtained by having a cell or microorganism introduced with a recombinant vector which contains DNA encoding a modified epimorphin comprising a functional domain which is a fragment of epimorphin comprising the 99th to 189th amino acids from the N-terminus of human epimorphin whose amino acid sequence is set forth in SEQ ID NO: 1 or the 100th to 190th amino acids from the N-terminus of mouse epimorphin whose amino acid sequence is set forth in SEQ ID NO: 4, wherein said functional domain promotes cell adhesion;
adding IPTG to induce expression of the modified epimorphin;
recovering the transformant;
lysing the transformant; and
obtaining the modified epimorphin from the resultant lysate.

58. The method according to claim 57 for producing a human modified epimorphin, which comprises using a transformant obtained by introducing a recombinant vector containing DNA encoding a human modified epimorphin having any one of SEQ ID NOS: 7 to 9 to a cell or microorganism.

59. The method according to claim 57 for producing a mouse modified epimorphin, which comprises using a transformant obtained by introducing a recombinant vector containing DNA encoding a human modified epimorphin having any one of SEQ ID NOS: 11 to 13 to a cell or microorganism.

60. A variant modified epimorphin comprising a functional domain which is a fragment of epimorphin comprising the 99th to 189th amino acids from the N-terminus of human epimorphin whose amino acid sequence is set forth in SEQ ID NO: 1, or the 100th to 190th amino acids from the N-terminus of mouse epimorphin whose amino acid sequence is set forth in SEQ ID NO: 4, wherein one or plural amino acid/acids selected from the following group A or B is/are substituted:
Group A: 111th, 114th, 126th, 129th, 130th, 132nd, 133rd, 138th, 144th, 148th, 153rd, 154th, 161st, 165th, 170th, 174th, 176th, 177th, 178th and 179th amino acids SEQ ID NO: 1; and
Group B: 112th, 115th, 127th, 130th, 131st, 133rd, 134th, 139th, 145th, 149th, 154th, 155th, 162nd, 166th, 171st, 175th, 177th, 178th, 179th and 180th amino acids SEQ ID NO: 4.

61. The variant modified epimorphin according to claim 60, wherein one or plural amino acid/acids selected from the group consisting of the following amino acids is/are substituted:
Asp of 111th amino acid of SEQ ID NO: 1 substituted with Gly,
Ile of 114th amino acid of SEQ ID NO: 1 substituted with Val or Leu,
Phe of 126th amino acid of SEQ ID NO: 1 substituted with Leu,
Met of 130th amino acid of SEQ ID NO: 1 substituted with Thr or Val,
Glu of 132nd amino acid of SEQ ID NO: 1 substituted with Val,
Tyr of 133rd amino acid of SEQ ID NO: 1 substituted with Phe, Ser of 144th amino acid of SEQ ID NO: 1 substituted with Gly, Ile of 148th amino acid of SEQ ID NO: 1 substituted with Val, Glu of 153rd amino acid of SEQ ID NO: 1 substituted with Val, Ile of 154th amino acid of SEQ ID NO: 1 substituted with Asn or Phe, Asp of 161st amino acid of SEQ ID NO: 1 substituted with Gly, Glu of 165th amino acid of SEQ ID NO: 1 substituted with Asp, Ser of 170th amino acid of SEQ ID NO: 1 substituted with Gly, Ser of 174th amino acid of SEQ ID NO: 1 substituted with Pro or Thr, Phe of 176th amino acid of SEQ ID NO: 1 substituted with Leu or Ser, Ser of 178th amino acid of SEQ ID NO: 1 substituted with Pro, and Asp of 179th amino acid of SEQ ID NO: 1 substituted with Gly.

62. The variant modified epimorphin according to claim 60, wherein one or plural amino acid/acids selected from the group consisting of the following amino acids is/are substituted:

Asp of 112th amino acid of SEQ ID NO: 4 substituted with Gly,

Ile of 115th amino acid of SEQ ID NO: 4 substituted with Val or Leu,

Phe of 127th amino acid of SEQ ID NO: 4 substituted with Leu,

Val of 130th amino acid of SEQ ID NO: 4 substituted with Ala,

Met of 131st amino acid of SEQ ID NO: 4 substituted with Thr or Val,

Glu of 133rd amino acid of SEQ ID NO: 4 substituted with Val,

Tyr of 134th amino acid of SEQ ID NO: 4 substituted with Phe,

Ile of 139th amino acid of SEQ ID NO: 4 substituted with Val,

Ser of 145th amino acid of SEQ ID NO: 4 substituted with Gly,

Ile of 149th amino acid of SEQ ID NO: 4 substituted with Val,

Glu of 154th amino acid of SEQ ID NO: 4 substituted with Val,

Ile of 155th amino acid of SEQ ID NO: 4 substituted with Asn or Phe,

Asp of 162nd amino acid of SEQ ID NO: 4 substituted with Gly,

Glu of 166th amino acid of SEQ ID NO: 4 substituted with Asp,

Ser of 171st amino acid of SEQ ID NO: 4 substituted with Gly,

Ser of 175th amino acid of SEQ ID NO: 4 substituted with Pro or Thr,

Phe of 177th amino acid of SEQ ID NO: 4 substituted with Leu or Ser,

Ile of 178th amino acid of SEQ ID NO: 4 substituted with Thr,

Ser of 179th amino acid of SEQ ID NO: 4 substituted with Pro, and

Asp of 180th amino acid of SEQ ID NO: 4 substituted with Gly.

63. The variant modified epimorphin according to claim 60 selected from the group consisting of the following variant modified epimorphin A, B, C, D, E and F:

A: a variant modified epimorphin obtained by
substituting Val for Ile of 148th amino acid of SEQ ID NO: 1, and
substituting Pro for Ser of 174th amino acid of SEQ ID NO: 1;

B: a variant modified epimorphin obtained by
substituting Thr for Ser of 174th amino acid of SEQ ID NO: 1;

C: a variant modified epimorphin obtained by
substituting Val for Ile of 114th amino acid of SEQ ID NO: 1,
substituting Leu for Phe of 126th amino acid of SEQ ID NO: 1,
substituting Thr for Met of 130th amino acid of SEQ ID NO: 1,
substituting Val for Glu of 153rd amino acid of SEQ ID NO: 1,
substituting Asp for Glu of 165th amino acid of SEQ ID NO: 1, and
substituting Leu for Phe of 176th amino acid of SEQ ID NO: 1;

D: a variant modified epimorphin obtained by
substituting Phe for Tyr of 133rd amino acid of SEQ ID NO: 1,
substituting Gly for Ser of 170th amino acid of SEQ ID NO: 1,
substituting Pro for Ser of 178th amino acid of SEQ ID NO: 1, and
substituting Gly for Asp of 179th amino acid of SEQ ID NO: 1;

E: a variant modified epimorphin obtained by
substituting Val for Glu of 132nd amino acid of SEQ ID NO: 1,
substituting Gly for Ser of 144th amino acid of SEQ ID NO: 1,
substituting Asn for Ile of 154th amino acid of SEQ ID NO: 1,
substituting Gly for Asp of 161st amino acid of SEQ ID NO: 1,
substituting Ser for Phe of 176th amino acid of SEQ ID NO: 1; and F: a variant modified epimorphin obtained by
substituting Gly for Asp of 111th amino acid of SEQ ID NO: 1,
substituting Leu for Ile of 114th amino acid of SEQ ID NO: 1,
substituting Val for Met of 130th amino acid of SEQ ID NO: 1, and
substituting Phe for Ile of 154th amino acid of SEQ ID NO: 1.

64. The variant modified epimorphin according to claim 60 selected from the group consisting of the following variant modified epimorphin A, B, C, D, E and F:

A: a variant modified epimorphin obtained by
substituting Val for Ile of 149th amino acid of SEQ ID NO: 4, and
substituting Pro for Ser of 175th amino acid of SEQ ID NO: 4;

B: a variant modified epimorphin obtained by
  substituting Thr for Ser of 175th amino acid of SEQ ID NO: 4;
C: a variant modified epimorphin obtained by
  substituting Val for Ile of 115th amino acid of SEQ ID NO: 4,
  substituting Leu for Phe of 127th amino acid of SEQ ID NO: 4,
  substituting Ala for Val of 130th amino acid of SEQ ID NO: 4,
  substituting Thr for Met of 131st amino acid of SEQ ID NO: 4,
  substituting Val for Ile of 139th amino acid of SEQ ID NO: 4,
  substituting Val for Glu of 154th amino acid of SEQ ID NO: 4,
  substituting Asp for Glu of 166th amino acid of SEQ ID NO: 1, and
  substituting Leu for Phe of 177th amino acid of SEQ ID NO: 4;
D: a variant modified epimorphin obtained by
  substituting Phe for Tyr of 134th amino acid of SEQ ID NO: 4,
  substituting Gly for Ser of 171st amino acid of SEQ ID NO: 4,
  substituting Thr for Ile of 178th amino acid of SEQ ID NO: 4,
  substituting Pro for Ser of 179th amino acid of SEQ ID NO: 4, and
  substituting Gly for Asp of 180th amino acid of SEQ ID NO: 4;
E: a variant modified epimorphin obtained by
  substituting Val for Glu of 133rd amino acid of SEQ ID NO: 4,
  substituting Gly for Ser of 145th amino acid of SEQ ID NO: 4,
  substituting Asn for Ile of 155th amino acid of SEQ ID NO: 4,
  substituting Gly for Asp of 162nd amino acid of SEQ ID NO: 4,
  substituting Ser for Phe of 177th amino acid of SEQ ID NO: 4; and
F: a variant modified epimorphin obtained by
  substituting Gly for Asp of 112th amino acid of SEQ ID NO: 4,
  substituting Leu for Ile of 115th amino acid of SEQ ID NO: 4,
  substituting Val for Met of 131st amino acid of SEQ ID NO: 4, and
  substituting Phe for Ile of 155th amino acid of SEQ ID NO: 4.

* * * * *

UNITED STATES PATENT AND TRADEMARK OFFICE
CERTIFICATE OF CORRECTION

PATENT NO. : 6,127,149
DATED : October 3, 2000
INVENTOR(S) : Yohei Hirai, et al.

It is certified that error appears in the above-identified patent and that said Letters Patent is hereby corrected as shown below:

Claim 1, column 51,
Line 20, change "100th or 190th" to -- 100th to 190th --;
Line 22, change "function" to -- functional --;

Claim 14, column 52,
Line 22, change "claim 7" to -- claim 1 --.

Signed and Sealed this

Thirtieth Day of October, 2001

Attest:

NICHOLAS P. GODICI
Attesting Officer    Acting Director of the United States Patent and Trademark Office

```
                      SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Met Arg Asp Arg Leu Pro Asp Leu Thr Ala Cys Arg Lys Asn Asp Asp
1               5                   10                  15

Gly Asp Thr Val Val Val Val Glu Lys Asp His Phe Met Asp Asp Phe
            20                  25                  30

Phe His Gln Val Glu Glu Ile Arg Asn Ser Ile Asp Lys Ile Thr Gln
                35                  40                  45

Tyr Val Glu Glu Val Lys Lys Asn His Ser Ile Ile Leu Ser Ala Pro
    50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Ala Lys Leu Lys Ala Ile Glu
                85                  90                  95

Gln Ser Phe Asp Gln Asp Glu Ser Gly Asn Arg Thr Ser Val Asp Leu
                100                 105                 110

Arg Ile Arg Arg Thr Gln His Ser Val Leu Ser Arg Lys Phe Val Glu
```

-continued

```
            115                 120                 125
Ala Met Ala Glu Tyr Asn Glu Ala Gln Thr Leu Phe Arg Glu Arg Ser
        130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
                180                 185                 190

Glu Ile Glu Ser Arg His Lys Asp Ile Met Lys Leu Glu Thr Ser Ile
            195                 200                 205

Arg Glu Leu His Glu Met Phe Met Asp Met Ala Met Phe Val Glu Thr
        210                 215                 220

Gln Gly Glu Met Ile Asn Asn Ile Glu Arg Asn Val Met Asn Ala Thr
225                 230                 235                 240

Asp Tyr Val Glu His Ala Lys Glu Thr Lys Lys Ala Ile Lys Thr
                245                 250                 255

Gln Ser Lys Ala Arg Arg Lys Lys Trp Ile Ile Ile Ala Val Ser Val
            260                 265                 270

Val Leu Val Val Ile Ile Val Leu Ile Ile Gly Leu Ser Val Gly Lys
        275                 280                 285
```

(2) INFORMATION FOR SEQ ID NO:2:

(i) SEQUENCE CHARACTERISTICS:
        (A) LENGTH: 287 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Arg Asp Arg Leu Pro Asp Leu Thr Ala Cys Arg Lys Asn Asp Asp
1               5                   10                  15

Gly Asp Thr Val Val Val Glu Lys Asp His Phe Met Asp Asp Phe
                20                  25                  30

Phe His Gln Val Glu Glu Ile Arg Asn Ser Ile Asp Lys Ile Thr Gln
            35                  40                  45

Tyr Val Glu Glu Val Lys Lys Asn His Ser Ile Ile Leu Ser Ala Pro
    50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Ala Lys Leu Lys Ala Ile Glu
                85                  90                  95

Gln Ser Phe Asp Gln Asp Glu Ser Gly Asn Arg Thr Ser Val Asp Leu
            100                 105                 110

Arg Ile Arg Arg Thr Gln His Ser Val Leu Ser Arg Lys Phe Val Glu
        115                 120                 125

Ala Met Ala Glu Tyr Asn Glu Ala Gln Thr Leu Phe Arg Glu Arg Ser
        130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
```

```
            180                 185                 190
Glu Ile Glu Ser Arg His Lys Asp Ile Met Lys Leu Glu Thr Ser Ile
            195                 200                 205
Arg Glu Leu His Glu Met Phe Met Asp Met Ala Met Phe Val Glu Thr
            210                 215                 220
Gln Gly Glu Met Ile Asn Asn Ile Glu Arg Asn Val Met Asn Ala Thr
225                 230                 235                 240
Asp Tyr Val Glu His Ala Lys Glu Glu Thr Lys Lys Ala Ile Lys Thr
            245                 250                 255
Gln Ser Lys Ala Arg Arg Lys Leu Met Phe Ile Ile Ile Cys Val Ile
            260                 265                 270
Val Leu Leu Val Ile Leu Gly Ile Ile Leu Ala Thr Thr Leu Ser
            275                 280                 285

(2) INFORMATION FOR SEQ ID NO:3:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met Arg Asp Arg Leu Pro Asp Leu Thr Ala Cys Arg Lys Asn Asp Asp
1               5                   10                  15
Gly Asp Thr Val Val Val Glu Lys Asp His Phe Met Asp Asp Phe
                20                  25                  30
Phe His Gln Val Glu Glu Ile Arg Asn Ser Ile Asp Lys Ile Thr Gln
            35                  40                  45
Tyr Val Glu Glu Val Lys Lys Asn His Ser Ile Ile Leu Ser Ala Pro
50                  55                  60
Asn Pro Glu Gly Lys Ile Lys Glu Glu Leu Glu Asp Leu Asn Lys Glu
65                  70                  75                  80
Ile Lys Lys Thr Ala Asn Lys Ile Arg Ala Lys Leu Lys Ala Ile Glu
            85                  90                  95
Gln Ser Phe Asp Gln Asp Glu Ser Gly Asn Arg Thr Ser Val Asp Leu
            100                 105                 110
Arg Ile Arg Arg Thr Gln His Ser Val Leu Ser Arg Lys Phe Val Glu
            115                 120                 125
Ala Met Ala Glu Tyr Asn Glu Ala Gln Thr Leu Phe Arg Glu Arg Ser
            130                 135                 140
Lys Gly Arg Ile Gln Arg Gln Leu Glu Ile Thr Gly Arg Thr Thr Thr
145                 150                 155                 160
Asp Asp Glu Leu Glu Glu Met Leu Glu Ser Gly Lys Pro Ser Ile Phe
                165                 170                 175
Thr Ser Asp Ile Ile Ser Asp Ser Gln Ile Thr Arg Gln Ala Leu Asn
                180                 185                 190
Glu Ile Glu Ser Arg His Lys Asp Ile Met Lys Leu Glu Thr Ser Ile
            195                 200                 205
Arg Glu Leu His Glu Met Phe Met Asp Met Ala Met Phe Val Glu Thr
            210                 215                 220
Gln Gly Glu Met Ile Asn Asn Ile Glu Arg Asn Val Met Asn Ala Thr
225                 230                 235                 240
Asp Tyr Val Glu His Ala Lys Glu Glu Thr Lys Lys Ala Ile Lys Tyr
```

-continued

```
                    245                 250                 255
Gln Ser Lys Ala Arg Arg Gln His Cys His Ser Asn His Ile Pro
            260                 265                 270

Arg Ala Ile Tyr Pro
            275
```

(2) INFORMATION FOR SEQ ID NO:4:

(i) SEQUENCE CHARACTERISTICS:
        (A) LENGTH: 289 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Arg Asp Arg Leu Pro Asp Leu Thr Ala Cys Arg Thr Asn Asp Asp
1               5                   10                  15

Gly Asp Thr Ala Val Val Ile Val Glu Lys Asp His Phe Met Asp Gly
            20                  25                  30

Phe Phe His Gln Val Glu Glu Ile Arg Ser Ser Ile Ala Arg Ile Ala
            35                  40                  45

Gln His Val Glu Asp Val Lys Lys Asn His Ser Ile Ile Leu Ser Ala
        50                  55                  60

Pro Asn Pro Glu Gly Lys Ile Lys Glu Leu Glu Asp Leu Asn Lys
65                  70                  75                  80

Glu Ile Lys Lys Thr Ala Asn Arg Ile Arg Gly Lys Leu Lys Ser Ile
                85                  90                  95

Glu Gln Ser Cys Asp Gln Asp Glu Asn Gly Asn Arg Thr Ser Val Asp
            100                 105                 110

Leu Arg Ile Arg Arg Thr Gln His Ser Val Leu Ser Arg Lys Phe Val
            115                 120                 125

Asp Val Met Thr Glu Tyr Asn Glu Ala Gln Ile Leu Phe Arg Glu Arg
        130                 135                 140

Ser Lys Gly Arg Ile Gln Arg Gln Leu Glu Ile Thr Gly Arg Thr Thr
145                 150                 155                 160

Thr Asp Asp Glu Leu Glu Glu Met Leu Glu Ser Gly Lys Pro Ser Ile
                165                 170                 175

Phe Ile Ser Asp Ile Ile Ser Asp Ser Gln Ile Thr Arg Gln Ala Leu
            180                 185                 190

Asn Glu Ile Glu Ser Arg His Lys Asp Ile Met Lys Leu Glu Thr Ser
        195                 200                 205

Ile Arg Glu Leu His Glu Met Phe Met Asp Met Ala Met Phe Val Glu
210                 215                 220

Thr Gln Gly Glu Met Val Asn Asn Ile Glu Arg Asn Val Val Asn Ser
225                 230                 235                 240

Val Asp Tyr Val Glu His Ala Lys Glu Glu Thr Lys Lys Ala Ile Lys
                245                 250                 255

Tyr Gln Ser Lys Ala Arg Arg Lys Lys Trp Ile Ile Ala Ala Val Ala
            260                 265                 270

Val Ala Val Ile Ala Val Leu Ala Leu Ile Ile Gly Leu Ser Val Gly
            275                 280                 285

Lys
```

(2) INFORMATION FOR SEQ ID NO:5:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Met Arg Asp Arg Leu Pro Asp Leu Thr Ala Cys Arg Thr Asn Asp Asp
1               5                   10                  15

Gly Asp Thr Ala Val Val Ile Val Glu Lys Asp His Phe Met Asp Gly
                20                  25                  30

Phe Phe His Gln Val Glu Glu Ile Arg Ser Ser Ile Ala Arg Ile Ala
            35                  40                  45

Gln His Val Glu Asp Val Lys Lys Asn His Ser Ile Ile Leu Ser Ala
        50                  55                  60

Pro Asn Pro Glu Gly Lys Ile Lys Glu Glu Leu Asp Leu Asn Lys
65                  70                  75                  80

Glu Ile Lys Lys Thr Ala Asn Arg Ile Arg Gly Lys Leu Lys Ser Ile
                85                  90                  95

Glu Gln Ser Cys Asp Gln Asp Glu Asn Gly Asn Arg Thr Ser Val Asp
            100                 105                 110

Leu Arg Ile Arg Arg Thr Gln His Ser Val Leu Ser Arg Lys Phe Val
        115                 120                 125

Asp Val Met Thr Glu Tyr Asn Glu Ala Gln Ile Leu Phe Arg Glu Arg
130                 135                 140

Ser Lys Gly Arg Ile Gln Arg Gln Leu Glu Ile Thr Gly Arg Thr Thr
145                 150                 155                 160

Thr Asp Asp Glu Leu Glu Glu Met Leu Glu Ser Gly Lys Pro Ser Ile
                165                 170                 175

Phe Ile Ser Asp Ile Ile Ser Asp Ser Gln Ile Thr Arg Gln Ala Leu
            180                 185                 190

Asn Glu Ile Glu Ser Arg His Lys Asp Ile Met Lys Leu Glu Thr Ser
        195                 200                 205

Ile Arg Glu Leu His Glu Met Phe Met Asp Met Ala Met Phe Val Glu
210                 215                 220

Thr Gln Gly Glu Met Val Asn Asn Ile Glu Arg Asn Val Val Asn Ser
225                 230                 235                 240

Val Asp Tyr Val Glu His Ala Lys Glu Glu Thr Lys Lys Ala Ile Lys
                245                 250                 255

Tyr Gln Ser Lys Ala Arg Arg Lys Val Met Phe Val Leu Ile Cys Val
            260                 265                 270

Val Thr Leu Leu Val Ile Leu Gly Ile Ile Leu Ala Thr Ala Leu Ser
        275                 280                 285

(2) INFORMATION FOR SEQ ID NO:6:

(i) SEQUENCE CHARACTERISTICS:
        (A) LENGTH: 279 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Met Arg Asp Arg Leu Pro Asp Leu Thr Ala Cys Arg Thr Asn Asp Asp

```
 1               5                   10                  15
Gly Asp Thr Ala Val Val Ile Val Glu Lys Asp His Phe Met Asp Gly
                20                  25                  30

Phe Phe His Gln Val Glu Glu Ile Arg Ser Ser Ile Ala Arg Ile Ala
            35                  40                  45

Gln His Val Glu Asp Val Lys Lys Asn His Ser Ile Ile Leu Ser Ala
        50                  55                  60

Pro Asn Pro Glu Gly Lys Ile Lys Glu Glu Leu Glu Asp Leu Asn Lys
 65              70                  75                  80

Glu Ile Lys Lys Thr Ala Asn Arg Ile Arg Gly Lys Leu Lys Ser Ile
                85                  90                  95

Glu Gln Ser Cys Asp Gln Asp Glu Asn Gly Asn Arg Thr Ser Val Asp
            100                 105                 110

Leu Arg Ile Arg Arg Thr Gln His Ser Val Leu Ser Arg Lys Phe Val
        115                 120                 125

Asp Val Met Thr Glu Tyr Asn Glu Ala Gln Ile Leu Phe Arg Glu Arg
130                 135                 140

Ser Lys Gly Arg Ile Gln Arg Gln Leu Glu Ile Thr Gly Arg Thr Thr
145                 150                 155                 160

Thr Asp Asp Glu Leu Glu Glu Met Leu Glu Ser Gly Lys Pro Ser Ile
                165                 170                 175

Phe Ile Ser Asp Ile Ile Ser Asp Ser Gln Ile Thr Arg Gln Ala Leu
            180                 185                 190

Asn Glu Ile Glu Ser Arg His Lys Asp Ile Met Lys Leu Glu Thr Ser
        195                 200                 205

Ile Arg Glu Leu His Glu Met Phe Met Asp Met Ala Met Phe Val Glu
210                 215                 220

Thr Gln Gly Glu Met Val Asn Asn Ile Glu Arg Asn Val Val Asn Ser
225                 230                 235                 240

Val Asp Tyr Val Glu His Ala Lys Glu Glu Thr Lys Lys Ala Ile Lys
                245                 250                 255

Tyr Gln Ser Lys Ala Arg Arg Gln Gln His Cys His Ser Asn Arg Thr
            260                 265                 270

Pro Arg Ala Leu Cys Pro Arg
        275
```

(2) INFORMATION FOR SEQ ID NO:7:

(i) SEQUENCE CHARACTERISTICS:
        (A) LENGTH: 711 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

```
ATGGATGATT TCTTCCATCA GGTGGAGGAG AATAGAAACA GTATTGATAA AATAACTCAA     60

TATGTTGAAG AAGTAAAGAA AAACCACAGC ATCATTCTTT CTGCACCAAA CCCGGAAGGA    120

AAAATAAAAG AAGAGCTTGA AGATCTGAAC AAAGAAATCA AGAAAATCGC GAATAAAATT    180

CGAGCCAAGT TAAAGGCTAT TGAACAAAGT TTTGATCAGG ATGAGAGTGG GAACCGGACT    240

TCAGTGGATC TTCGGATACG AAGAACCCAG CATTCGGTGC TGTCTCGGAA GTTTGTGGAA    300

GCCATGGCGG AGTACAATGA GGCACAGACT CTGTTTCGGG AGCGGAGCAA AGGCCGCATC    360

CAGCGCCAGC TGGAGATAAC TGGGAGAACC ACCACAGACG ACGAGCTAGA AGAGATGCTG    420
```

```
GAGAGCGGGA AGCCATCCAT CTTCACTTCC GACATTATAT CAGATTCACA AATTACTAGA      480

CAAGCTCTCA ATGAAATCGA GTCACGTCAC AAGGACATCA TGAAGCTGGA GACCAGCATC      540

CGAGAGTTGC ATGAGATGTT CATGGACATG GCTATGTTTG TGGAGACTCA GGGTGAAATG      600

ATCAACAACA TAGAAAGAAA TGTTATGAAT GCCACAGACT ATGTAGAACA CGCTAAAGAA      660

GAAACAAAAA AAGCTATCAA ATATCAGAGC AAGGCAAGAA GGAAAAAGTG A               711

(2) INFORMATION FOR SEQ ID NO:8:

(i) SEQUENCE CHARACTERISTICS:
         (A) LENGTH: 564 base pairs
         (B) TYPE: nucleic acid
         (C) STRANDEDNESS: double
         (D) TOPOLOGY: linear (ii) MOLECULE TYPE: cDNA (xi) SEQUENCE DESCRIPTION: SEQ ID NO:8:

AACAAAGAAA TCAAGAAAAC TGCGAATAAA ATTCGAGCCA AGTTAAAGGC TATTGAACAA       60

AGTTTTGATC AGGATGAGAG TGGGAACCGG ACTTCAGTGG ATCTTCGGAT ACGAAGAACC      120

CACCATTCGG TGCTGTCTCG GAAGTTTGTG GAAGCCATGG CGGAGTACAA TGAGGCACAG      180

ACTCTGTTTC GGGAGCGGAG CAAAGGCCGC ATCCAGCGCC AGCTGGAGAT AACTGGGAGA      240

ACCACCACAG ACGACGAGCT AGAAGAGATG CTGGAGAGCG GGAAGCCATC CATCTTCACT      300

TCCGACATTA TATCAGATTC ACAAATTACT AGACAAGCTC TCAATGAAAT CGAGTCACGT      360

CACAAGGACA TCATGAAGCT GGAGACCAGC ATCCGAGAGT TGCATGAGAT GTTCATGGAC      420

ATGGCTATGT TTGTGGAGAC TCAGGGTGAA ATGATCAACA ACATAGAAAG AAATGTTATG      480

AATGCCACAG ACTATGTAGA ACACGCTAAA GAAGAAACAA AAAAAGCTAT CAAATATCAG      540

AGCAAGGCAA GAAGGAAAAA GTGA                                             564

(2) INFORMATION FOR SEQ ID NO:9:

(i) SEQUENCE CHARACTERISTICS:
         (A) LENGTH: 486 base pairs
         (B) TYPE: nucleic acid
         (C) STRANDEDNESS: double
         (D) TOPOLOGY: linear (ii) MOLECULE TYPE: cDNA (xi) SEQUENCE DESCRIPTION: SEQ ID NO:9:

AGTGGGAACC GGACTTCAGT GGATCTTCGG ATACGAAGAA CCCAGCATTC GGTGCTGTCT       60

CGGAAGTTTG TGGAAGCCAT GGCGGAGTAC AATGAGGCAC AGACTCTGTT TCGGGAGCGG      120

AGCAAAGGCC GCATCCAGCG CCAGCTGGAG ATAACTGGGA GAACCACCAC AGACGACGAG      180

CTAGAAGAGA TGCTGGAGAG CGGGAAGCCA TCCATCTTCA CTTCCGACAT TATATCAGAT      240

TCACAAATTA CTAGACAAGC TCTCAATGAA ATCGAGTCAC GTCACAAGGA CATCATGAAG      300

CTGGAGACCA GCATCCGAGA GTTGCATGAG ATGTTCATGG ACATGGCTAT GTTTGTGGAG      360

ACTCAGGGTG AAATGATCAA CAACATAGAA AGAAATGTTA TGAATGCCAC AGACTATGTA      420

GAACACGCTA AGAAGAAAC AAAAAAAGCT ATCAAATATC AGAGCAAGGC AAGAAGGAAA       480

AAGTGA                                                                 486

(2) INFORMATION FOR SEQ ID NO:10:

(i) SEQUENCE CHARACTERISTICS:
```

(A) LENGTH: 795 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

ATGCGGGACC GGCTGCCAGA CCTGACGGCG TGTAGGAAGA ATGATGATGG AGACACAGTT      60

GTTGTGGTTG AGAAAGATCA TTTCATGGAT GATTTCTTCC ATCAGGTGGA GGAGATTAGA     120

AACAGTATTG ATAAAATAAC TCAATATGTT GAAGAAGTAA AGAAAAACCA CAGCATCATT     180

CTTTCTGCAC CAAACCCGGA AGGAAAAATA AAAGAAGAGC TTGAAGATCT GAACAAAGAA     240

ATCAAGAAAA CTGCGAATAA AATTCGAGCC AAGTTAAAGG CTATTGAACA AAGTTTTGAT     300

CAGGATGAGA GTGGGAACCG GACTTCAGTG GATCTTCGGA TACGAAGAAC CCAGCATTCG     360

GTGCTGTCTC GGAAGTTTGT GGAAGCCATG GCGGAGTACA ATGAGGCACA GACTCTGTTT     420

CGGGAGCGGA GCAAAGGCCG CATCCAGCGC CAGCTGGAGA TAACTGGGAG AACCACCACA     480

GACGACGAGC TAGAAGAGAT GCTGGAGAGC GGGAAGCCAT CCATCTTCAC TTCCGACATT     540

ATATCAGATT CACAAATTAC TAGACAAGCT CTCAATGAAA TCGAGTCACG TCACAAGGAC     600

ATCATGAAGC TGGAGACCAG CATCCGAGAG TTGCATGAGA TGTTCATGGA CATGGCTATG     660

TTTGTGGAGA CTCAGGGTGA ATGATCAAC AACATAGAAA GAAATGTTAT GAATGCCACA     720

GACTATGTAG AACACGCTAA AGAAGAAACA AAAAAAGCTA TCAAATATCA GAGCAAGGCA     780

AGAAGGAAAA AGTGA                                                     795

(2) INFORMATION FOR SEQ ID NO:11:

(i) SEQUENCE CHARACTERISTICS:
        (A) LENGTH: 711 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

ATGGACGGTT TCTTCCATCA GGTAGAGGAG ATTCGAAGCA GCATAGCCAG GATTGCTCAG      60

CATGTAGAAG ACGTGAAGAA GAACCACAGC ATCATCCTGT CTGCTCCAAA CCCAGAAGGA     120

AAAATAAAAG AAGAGCTGGA GGACCTGAAC AAAGAGATCA AGAAAACTGC TAACAGGATC     180

CGGGGCAAGC TGAAGTCTAT TGAGCAGAGC TGTGATCAGG ACGAGAATGG GAACCGAACT     240

TCAGTGGATC TGCGGATACG AAGGACCCAG CACTCGGTGC TGTCACGGAA GTTTGTGGAC     300

GTCATGACAG AATACAATGA AGCGCAGATC CTGTTCCGGG AGCGAAGCAA AGGCCGCATC     360

CAGCGCCAGC TGGAGATCAC TGGGAGGACC ACCACTGACG ACGAGCTGGA GAGATGCTG     420

GAGAGCGGGA AGCCGTCCAT CTTCATCTCG GATATTATAT CAGATTCACA AATCACTAGG     480

CAAGCTCTCA ATGAGATCGA GTCCCGCCAC AAAGACATCA TGAAGCTGGA GACCAGCATC     540

CGAGAGCTGC ACGAGATGTT CATGGATATG GCCATGTTTG TCGAGACTCA GGGTGAAATG     600

GTCAACAACA TCGAGAGAAA TGTGGTGAAC TCTGTAGATT ACGTGAACA TGCCAAGGAA     660

GAGACGAAGA AAGCCATCAA ATACCAGAGC AAGGCCAGGC GGAAAAAGTG A              711

(2) INFORMATION FOR SEQ ID NO:12:

(i) SEQUENCE CHARACTERISTICS:
        (A) LENGTH: 564 base pairs

```
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

AACAAAGAGA TCAAGAAAAC TGCTAACAGG ATCCGGGGCA AGCTGAAGTC TATTGAGCAG        60

AGCTGTGATC AGGACGAGAA TGGGAACCGA ACTTCAGTGG ATCTGCGGAT ACGAAGGACC       120

CAGCACTCGG TGCTGTCACG GAAGTTTGTG GACGTCATGA CAGAATACAA TGAAGCGCAG       180

ATCCTGTTCC GGGAGCGAAG CAAAGGCCGC ATCCAGCGCC AGCTGGAGAT CACTGGGAGG       240

ACCACCACTG ACGACGAGCT GGAAGAGATG CTGGAGAGCG GGAAGCCGTC CATCTTCATC       300

TCGGATATTA TATCAGATTC ACAAATCACT AGGCAAGCTC TCAATGAGAT CGAGTCCCGC       360

CACAAAGACA TCATGAAGCT GGAGACCAGC ATCCGAGAGC TGCACGAGAT GTTCATGGAT       420

ATGGCCATGT TTGTCGAGAC TCAGGGTGAA ATGGTCAACA CATCGAGAG AAATGTGGTG        480

AACTCTGTAG ATTACGTGGA ACATGCCAAG GAAGAGACGA AGAAAGCCAT CAAATACCAG       540

AGCAAGGCCA GGCGGAAAAA GTGA                                             564

(2) INFORMATION FOR SEQ ID NO:13:

(i) SEQUENCE CHARACTERISTICS:
        (A) LENGTH: 486 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

AATGGGAACC GAACTTCAGT GGATCTGCGG ATACGAAGGA CCCAGCACTC GGTGCTGTCA        60

CGGAAGTTTG TGGACGTCAT GACAGAATAC AATGAAGCGC AGATCCTGTT CCGGGAGCGA       120

AGCAAAGGCC GCATCCAGCG CCAGCTGGAG ATCACTGGGA GGACCACCAC TGACGACGAG       180

CTGGAAGAGA TGCTGGAGAG CGGGAAGCCG TCCATCTTCA TCTCGGATAT TATATCAGAT       240

TCACAAATCA CTAGGCAAGC TCTCAATGAG ATCGAGTCCC GCCACAAAGA CATCATGAAG       300

CTGGAGACCA GCATCCGAGA GCTGCACGAG ATGTTCATGG ATATGGCCAT GTTTGTCGAG       360

ACTCAGGGTG AAATGGTCAA CACATCGAG AGAAATGTGG TGAACTCTGT AGATTACGTG        420

GAACATGCCA AGGAAGAGAC GAAGAAAGCC ATCAAATACC AGAGCAAGGC CAGGCGGAAA       480

AAGTGA                                                                 486

(2) INFORMATION FOR SEQ ID NO:14:

(i) SEQUENCE CHARACTERISTICS:
        (A) LENGTH: 798 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

ATGCGGGACC GGCTGCCCGA CCTCACGGCG TGTAGGACAA ACGACGATGG AGACACTGCT        60

GTCGTCATTG TGGAGAAGGA TCATTTCATG ACGGTTTCT TCCATCAGGT AGAGGAGATT        120

CGAAGCAGCA TAGCCAGGAT TGCTCAGCAT GTAGAAGACG TGAAGAAGAA CCACAGCATC       180

ATCCTGTCTG CTCCAAACCC AGAAGGAAAA ATAAAAGAAG AGCTGGAGGA CCTGGACAAA       240
```

-continued

```
GAGATCAAGA AAACTGCTAA CAGGATCCGG GGCAAGCTGA AGTCTATTGA GCAGAGCTGT    300

GATCAGGACG AGAATGGGAA CCGAACTTCA GTGGATCTGC GGATACGAAG ACCCAGCAC     360

TCGGTGCTGT CACGGAAGTT TGTGGACGTC ATGACAGAAT ACAATGAAGC GCAGATCCTG    420

TTCCGGGAGC GAAGCAAAGG CCGCATCCAG CGCCAGCTGG AGATCACTGG GAGGACCACC    480

ACTGACGACG AGCTGGAAGA GATGCTGGAG AGCGGGAAGC CGTCCATCTT CATCTCGGAT    540

ATTATATCAG ATTCACAAAT CACTAGGCAA GCTCTCAATG AGATCGAGTC CCGCCACAAA    600

GACATCATGA AGCTGGAGAC CAGCATCCGA GAGCTGCACG AGATGTTCAT GGATATGGCC    660

ATGTTTGTCG AGACTCAGGG TGAAATGGTC AACAACATCG AGAGAAATGT GGTGAACTCT    720

GTAGATTACG TGGAACATGC CAAGGAAGAG ACGAAGAAAG CCATCAAATA CCAGAGCAAG    780

GCCAGGCGGA AAAAGTGA                                                  798
```

(2) INFORMATION FOR SEQ ID NO:15:

(i) SEQUENCE CHARACTERISTICS:
        (A) LENGTH: 236 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Met Asp Asp Phe Phe His Gln Val Glu Glu Ile Arg Asn Ser Ile Asp
  1               5                  10                  15

Lys Ile Thr Gln Tyr Val Glu Val Lys Lys Asn His Ser Ile Ile
                 20                  25                  30

Leu Ser Ala Pro Asn Pro Glu Gly Lys Ile Lys Glu Glu Leu Glu Asp
             35                  40                  45

Leu Asn Lys Glu Ile Lys Lys Thr Ala Asn Lys Ile Arg Ala Lys Leu
         50                  55                  60

Lys Ala Ile Glu Gln Ser Phe Asp Gln Asp Glu Ser Gly Asn Arg Thr
 65                  70                  75                  80

Ser Val Asp Leu Arg Ile Arg Arg Thr Gln His Ser Val Leu Ser Arg
                 85                  90                  95

Lys Phe Val Glu Ala Met Ala Glu Tyr Asn Glu Ala Gln Thr Leu Phe
            100                 105                 110

Arg Glu Arg Ser Lys Gly Arg Ile Gln Arg Gln Leu Glu Ile Thr Gly
            115                 120                 125

Arg Thr Thr Thr Asp Asp Glu Leu Glu Glu Met Leu Glu Ser Gly Lys
        130                 135                 140

Pro Ser Ile Phe Thr Ser Asp Ile Ile Ser Asp Ser Gln Ile Thr Arg
145                 150                 155                 160

Gln Ala Leu Asn Glu Ile Glu Ser Arg His Lys Asp Ile Met Lys Leu
                165                 170                 175

Glu Thr Ser Ile Arg Glu Leu His Glu Met Phe Met Asp Met Ala Met
            180                 185                 190

Phe Val Glu Thr Gln Gly Glu Met Ile Asn Asn Ile Glu Arg Asn Val
            195                 200                 205

Met Asn Ala Thr Asp Tyr Val Glu His Ala Lys Glu Glu Thr Lys Lys
        210                 215                 220

Ala Ile Lys Thr Gln Ser Lys Ala Arg Arg Lys Lys
225                 230                 235
```

(2) INFORMATION FOR SEQ ID NO:16:

(i) SEQUENCE CHARACTERISTICS:
        (A) LENGTH: 187 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Asn Lys Glu Ile Lys Lys Thr Ala Asn Lys Ile Arg Ala Lys Leu Lys
 1               5                  10                  15

Ala Ile Glu Gln Ser Phe Asp Gln Asp Glu Ser Gly Asn Arg Thr Ser
            20                  25                  30

Val Asp Leu Arg Ile Arg Arg Thr Gln His Ser Val Leu Ser Arg Lys
        35                  40                  45

Phe Val Glu Ala Met Ala Glu Tyr Asn Glu Ala Gln Thr Leu Phe Arg
    50                  55                  60

Glu Arg Ser Lys Gly Arg Ile Gln Arg Gln Leu Glu Ile Thr Gly Arg
65                  70                  75                  80

Thr Thr Thr Asp Asp Glu Leu Glu Glu Met Leu Glu Ser Gly Lys Pro
                85                  90                  95

Ser Ile Phe Thr Ser Asp Ile Ile Ser Asp Ser Gln Ile Thr Arg Gln
            100                 105                 110

Ala Leu Asn Glu Ile Glu Ser Arg His Lys Asp Ile Met Lys Leu Glu
        115                 120                 125

Thr Ser Ile Arg Glu Leu His Glu Met Phe Met Asp Met Ala Met Phe
    130                 135                 140

Val Glu Thr Gln Gly Glu Met Ile Asn Asn Ile Glu Arg Asn Val Met
145                 150                 155                 160

Asn Ala Thr Asp Tyr Val Glu His Ala Lys Glu Glu Thr Lys Lys Ala
                165                 170                 175

Ile Lys Thr Gln Ser Lys Ala Arg Arg Lys Lys
            180                 185
```

(2) INFORMATION FOR SEQ ID NO:17:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Ser Gly Asn Arg Thr Ser Val Asp Leu Arg Ile Arg Arg Thr Gln His
 1               5                  10                  15

Ser Val Leu Ser Arg Lys Phe Val Glu Ala Met Ala Glu Tyr Asn Glu
            20                  25                  30

Ala Gln Thr Leu Phe Arg Glu Arg Ser Lys Gly Arg Ile Gln Arg Gln
        35                  40                  45

Leu Glu Ile Thr Gly Arg Thr Thr Thr Asp Asp Glu Leu Glu Glu Met
    50                  55                  60

Leu Glu Ser Gly Lys Pro Ser Ile Phe Thr Ser Asp Ile Ile Ser Asp
65                  70                  75                  80

Ser Gln Ile Thr Arg Gln Ala Leu Asn Glu Ile Glu Ser Arg His Lys
                85                  90                  95
```

```
Asp Ile Met Lys Leu Glu Thr Ser Ile Arg Glu Leu His Glu Met Phe
            100                 105                 110

Met Asp Met Ala Met Phe Val Glu Thr Gln Gly Glu Met Ile Asn Asn
            115                 120                 125

Ile Glu Arg Asn Val Met Asn Ala Thr Asp Tyr Val Glu His Ala Lys
            130                 135                 140

Glu Glu Thr Lys Lys Ala Ile Lys Thr Gln Ser Lys Ala Arg Arg Lys
145                 150                 155                 160

Lys (2) INFORMATION FOR SEQ ID NO:18:

(i) SEQUENCE CHARACTERISTICS:
        (A) LENGTH: 236 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Met Asp Gly Phe Phe His Gln Val Glu Glu Ile Arg Ser Ser Ile Ala
1               5                   10                  15

Arg Ile Ala Gln His Val Glu Asp Val Lys Lys Asn His Ser Ile Ile
            20                  25                  30

Leu Ser Ala Pro Asn Pro Glu Gly Lys Ile Lys Glu Glu Leu Glu Asp
            35                  40                  45

Leu Asn Lys Glu Ile Lys Lys Thr Ala Asn Arg Ile Arg Gly Lys Leu
50                  55                  60

Lys Ser Ile Glu Gln Ser Cys Asp Gln Asp Glu Asn Gly Asn Arg Thr
65                  70                  75                  80

Ser Val Asp Leu Arg Ile Arg Arg Thr Gln His Ser Val Leu Ser Arg
            85                  90                  95

Lys Phe Val Asp Val Met Thr Glu Tyr Asn Glu Ala Gln Ile Leu Phe
            100                 105                 110

Arg Glu Arg Ser Lys Gly Arg Ile Gln Arg Gln Leu Glu Ile Thr Gly
            115                 120                 125

Arg Thr Thr Thr Asp Asp Glu Leu Glu Glu Met Leu Glu Ser Gly Lys
            130                 135                 140

Pro Ser Ile Phe Ile Ser Asp Ile Ile Ser Asp Ser Gln Ile Thr Arg
145                 150                 155                 160

Gln Ala Leu Asn Glu Ile Glu Ser Arg His Lys Asp Ile Met Lys Leu
            165                 170                 175

Glu Thr Ser Ile Arg Glu Leu His Glu Met Phe Met Asp Met Ala Met
            180                 185                 190

Phe Val Glu Thr Gln Gly Glu Met Val Asn Asn Ile Glu Arg Asn Val
            195                 200                 205

Val Asn Ser Val Asp Tyr Val Glu His Ala Lys Glu Glu Thr Lys Lys
            210                 215                 220

Ala Ile Lys Tyr Gln Ser Lys Ala Arg Arg Lys Lys
225                 230                 235

(2) INFORMATION FOR SEQ ID NO:19:

(i) SEQUENCE CHARACTERISTICS:
        (A) LENGTH: 187 amino acids
        (B) TYPE: amino acid
```

```
            (C) STRANDEDNESS: single
            (D) TOPOLOGY: linear (ii) MOLECULE TYPE: peptide (xi) SEQUENCE DESCRIPTION: SEQ ID NO:19:

Asn Lys Glu Ile Lys Lys Thr Ala Asn Arg Ile Arg Gly Lys Leu Lys
1               5                   10                  15

Ser Ile Glu Gln Ser Cys Asp Gln Asp Glu Asn Gly Asn Arg Thr Ser
                20                  25                  30

Val Asp Leu Arg Ile Arg Arg Thr Gln His Ser Val Leu Ser Arg Lys
                35                  40                  45

Phe Val Asp Val Met Thr Glu Tyr Asn Glu Ala Gln Ile Leu Phe Arg
50                      55                  60

Glu Arg Ser Lys Gly Arg Ile Gln Arg Gln Leu Glu Ile Thr Gly Arg
65                  70                  75                  80

Thr Thr Thr Asp Asp Glu Leu Glu Glu Met Leu Glu Ser Gly Lys Pro
                85                  90                  95

Ser Ile Phe Ile Ser Asp Ile Ile Ser Asp Ser Gln Ile Thr Arg Gln
                100                 105                 110

Ala Leu Asn Glu Ile Glu Ser Arg His Lys Asp Ile Met Lys Leu Glu
                115                 120                 125

Thr Ser Ile Arg Glu Leu His Glu Met Phe Met Asp Met Ala Met Phe
130                 135                     140

Val Glu Thr Gln Gly Glu Met Val Asn Asn Ile Glu Arg Asn Val Val
145                 150                 155                 160

Asn Ser Val Asp Tyr Val Glu His Ala Lys Glu Glu Thr Lys Lys Ala
                165                 170                 175

Ile Lys Tyr Gln Ser Lys Ala Arg Arg Lys Lys
                180                 185

(2) INFORMATION FOR SEQ ID NO:20:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Asn Gly Asn Arg Thr Ser Val Asp Leu Arg Ile Arg Arg Thr Gln His
1               5                   10                  15

Ser Val Leu Ser Arg Lys Phe Val Asp Val Met Thr Glu Tyr Asn Glu
                20                  25                  30

Ala Gln Ile Leu Phe Arg Glu Arg Ser Lys Gly Arg Ile Gln Arg Gln
                35                  40                  45

Leu Glu Ile Thr Gly Arg Thr Thr Thr Asp Asp Glu Leu Glu Glu Met
50                      55                  60

Leu Glu Ser Gly Lys Pro Ser Ile Phe Ile Ser Asp Ile Ile Ser Asp
65                  70                  75                  80

Ser Gln Ile Thr Arg Gln Ala Leu Asn Glu Ile Glu Ser Arg His Lys
                85                  90                  95

Asp Ile Met Lys Leu Glu Thr Ser Ile Arg Glu Leu His Glu Met Phe
                100                 105                 110

Met Asp Met Ala Met Phe Val Glu Thr Gln Gly Glu Met Val Asn Asn
                115                 120                 125
```

```
Ile Glu Arg Asn Val Val Asn Ser Val Asp Tyr Val Glu His Ala Lys
    130                 135                 140
Glu Glu Thr Lys Lys Ala Ile Lys Tyr Gln Ser Lys Ala Arg Arg Lys
145                 150                 155                 160
Lys
```

(2) INFORMATION FOR SEQ ID NO:21:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Tyr Pro Tyr Asp Val Pro Asp Tyr Ala
1               5
```

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Glu Gln Lys Leu Ile Ser Glu Glu Asp Leu Asn
1               5                   10
```

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Glu Tyr Lys Glu Glu Glu Glu Lys
1               5
```

(2) INFORMATION FOR SEQ ID NO:24:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Tyr Thr Asp Ile Glu Met Asn Arg Leu Gly Lys
1               5                   10
```

(2) INFORMATION FOR SEQ ID NO:25:

(i) SEQUENCE CHARACTERISTICS:
        (A) LENGTH: 15 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:25:

Arg Ile Gln Arg Gly Pro Gly Arg Ala Phe Val Thr Ile Gly Lys
1               5                   10                  15

(2) INFORMATION FOR SEQ ID NO:26:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Ala Ser Met Thr Gly Gly Gln Gln Met Gly Arg
1               5                   10

(2) INFORMATION FOR SEQ ID NO:27:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Gln Pro Glu Leu Ala Pro Glu Asp Pro Glu Asp
1               5                   10

(2) INFORMATION FOR SEQ ID NO:28:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Gly Ala Pro Val Pro Tyr Asp Pro Leu Glu Pro Arg
1               5                   10

(2) INFORMATION FOR SEQ ID NO:29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

ATGCGGGACC GGCTG                                                15

(2) INFORMATION FOR SEQ ID NO:30:

(i) SEQUENCE CHARACTERISTICS:
        (A) LENGTH: 15 base pairs
        (B) TYPE: nucleic acid
```

-continued

```
        (C) STRANDEDNESS: single
        (D) TOPOLOGY: linear (ii) MOLECULE TYPE: cDNA (xi) SEQUENCE DESCRIPTION: SEQ ID NO:30:

TCATTTGCCA ACCGA                                                         15
```